(12) United States Patent
Barban

(10) Patent No.: US 6,284,249 B1
(45) Date of Patent: Sep. 4, 2001

(54) FUSION POLYPEPTIDE HAVING THE C PROTEIN AND E1 PROTEIN OF HEPATITIS C VIRUS

(75) Inventor: Véronique Barban, Lyons (FR)

(73) Assignee: Pasteur Merieux Sérums & Vaccins, Lyons (FR)

( * ) Notice: Subject to any disclaimer, the term of this patent is extended or adjusted under 35 U.S.C. 154(b) by 0 days.

(21) Appl. No.: 09/388,874

(22) Filed: Sep. 2, 1999

Related U.S. Application Data

(63) Continuation-in-part of application No. PCT/FR98/00448, filed on Mar. 6, 1998.

(30) Foreign Application Priority Data

Mar. 6, 1997 (FR) .................................................. 97/02887

(51) Int. Cl.⁷ .................................................. A61K 39/00
(52) U.S. Cl. .................................... 424/192.1; 424/185.1; 424/186.1; 424/189.1; 435/5; 435/91.32; 435/173.3; 435/236; 435/320.1; 514/934; 530/300; 530/350; 530/826; 536/23.4; 536/23.72
(58) Field of Search .............................. 424/185.1, 186.1, 424/189.1, 192.1; 435/5, 91.32, 173.3, 236, 320.1; 514/934; 530/300, 350, 826; 536/23.5, 23.4, 23.72

(56) References Cited

U.S. PATENT DOCUMENTS

| | | | |
|---|---|---|---|
| 5,645,983 | * | 7/1997 | Liao et al. ............................... 435/5 |
| 5,747,339 | * | 5/1998 | Okayama et al. .................... 435/350 |

FOREIGN PATENT DOCUMENTS

| | | |
|---|---|---|
| 0 484 787 A | 5/1992 | (EP) . |
| 97/02887 | 3/1997 | (FR) . |
| WO 98/39030 | 9/1998 | (WO) . |

OTHER PUBLICATIONS

Choo, et al., "Genetic organization and diversity of the hepatitis C virus", *PNAS*, 88:2451–2455 (1991).

Takeuchi, K., et al., "Nucleotide sequence of core and envelope genes of the hepatitis C virus genome derived directly from human healthy carriers," *Nucleic Acid Research*, 18:4626 (1990).

Houghton, M., et al., "Molecular Biology of the Hepatitis C Viruses: Implications for Diagnosis, Development and Control of Viral Disease," *Hepatology*, 14:381–388 (1991).

Delisse, et al., "Sequence analysis of the putative structural genes of hepatitis C virus from Japanese and European origin," *J Hepatology*, 13(Suppl 4):S20–S23 (1991).

Bukh, J., et al., "Sequence analysis of the core gene of 14 hepatitis C virus genotypes", *PNAS*, 91:8239–8243 (1994).

Okamoto, H., et al., "Genetic Heterogeneity of Hepatitis C Virus," *Intervirology*, 37:68–76 (1994).

Grakoui, et al., "Expression and Identification of Hepatitis C Virus Polyprotein Cleavage Products," *J Virol*, 67:1385–1395 (1993).

Spaete, et al. "Characterization of the Hepatitis C Virus E2/NS1 Gene Product Expressed in Mammalian Cells," *Virology*, 188:819–830 (1992).

Matsuura, et al., "Expression of Processed Envelope Protein of Hepatitis C in Mammalian and Insect Cells," *J Virol*, 66:1425–1431 (1992).

Kohara, M., et al., "Expression and characterization of glycoprotein gp35 of hepatitis C virus using recombinant vaccinia virus," *J Gen Virol*, 73:2313–2318 (1992).

Liu, Q., et al., "Regulated processing of hepatitis C virus core protein is linked to subcellular localization", *J Virol*, 71(1):657–662 (1997).

Hussy, P., et al., Hepatitis C virus core protein: Carboxy–terminal boundaries of a signal peptide peptidase, *Virology*, 224(1):93–104 (1993).

\* cited by examiner

*Primary Examiner*—Jeffrey Stucker
*Assistant Examiner*—Ulrike Winkler
(74) *Attorney, Agent, or Firm*—Hamilton, Brook, Smith & Reynolds, P.C.

(57) ABSTRACT

The invention concerns a pharmaceutical composition for treating or preventing C hepatitis (HCV), induced infections, which in a preferred embodiment, comprises a main active principle, (i) a fusion polypeptide, including the HCV capsid polypeptide (C191) and polypeptide coat (E1) and in which at least one cleavage site 173/174 and 191/192 has been made inoperative by mutation; (ii) an equimolar mixture of the C191 polypeptide of which the cleavage site 173/174 has been made inoperative and of the E1 polypeptide (mixture equivalent to the fusion polypeptide); or (iii) a DNA molecule coding for this fusion polypeptide. Products (i) to (iii) are characterized in that the C191 element is incapable of regulating the functioning of the genes, in particular of causing them to interact. Such a composition can also include any form equivalent to the products described above.

15 Claims, 15 Drawing Sheets

```
cactccacca tgaatcactc ccctgtgagg aactactgtc ttcacgcaga aagcgtctag    60
ccatggcgtt agtatgagtg tcgtgcagcc tccaggaccc ccctcccgg gagagccata   120
gtggtctgcg gaaccggtga gtacaccgga attgccagga cgaccgggtc ctttcttgga   180
tcaacccgct caatgcctgg agatttgggc gtgccccgc aagactgcta gccgagtagt   240
gttgggtcgc gaaaggcctt gtggtactgc ctgataggg gcttgcgagt gccccgggag   300
gtctcgtaga ccgtgcacc atg agc acg aat cct aaa cct caa aaa aaa aac   352
                     Met Ser Thr Asn Pro Lys Pro Gln Lys Lys Asn
                      1               5                   10
```

```
aaa cgt aac acc aac cgt cgc cca cag gac gtc aag ttc ccg ggt ggc    400
Lys Arg Asn Thr Asn Arg Arg Pro Gln Asp Val Lys Phe Pro Gly Gly
             15                  20                  25 ggt cag atc gtt ggt gga gtt tac ttg ttg ccg cgc agg ggc cct aga    448
Gly Gln Ile Val Gly Gly Val Tyr Leu Leu Pro Arg Arg Gly Pro Arg
         30                  35                  40 ttg ggt gtg cgc gcg acg aga aag act tcc gag cgg tcg caa cct cga    496
Leu Gly Val Arg Ala Thr Arg Lys Thr Ser Glu Arg Ser Gln Pro Arg
     45                  50                  55 ggt aga cgt cag cct atc ccc aag gct cgt cgg ccc gag ggc agg acc    544
Gly Arg Arg Gln Pro Ile Pro Lys Ala Arg Arg Pro Glu Gly Arg Thr
 60                  65                  70                  75 tgg gct cag ccc ggg tac cct tgg ccc ctc tat ggc aat gag ggc tgc    592
Trp Ala Gln Pro Gly Tyr Pro Trp Pro Leu Tyr Gly Asn Glu Gly Cys
                 80                  85                  90 ggg tgg gcg gga tgg ctc ctg tct ccc cgt ggc tct cgg cct agc tgg    640
Gly Trp Ala Gly Trp Leu Leu Ser Pro Arg Gly Ser Arg Pro Ser Trp
             95                 100                 105 ggc ccc aca gac ccc cgg cgt agg tcg cgc aat ttg ggt aag gtc atc    688
Gly Pro Thr Asp Pro Arg Arg Arg Ser Arg Asn Leu Gly Lys Val Ile
         110                 115                 120 gat acc ctt acg tgc ggc ttc gcc gac ctc atg ggg tac ata ccg ctc    736
Asp Thr Leu Thr Cys Gly Phe Ala Asp Leu Met Gly Tyr Ile Pro Leu
     125                 130                 135 gtc ggc gcc cct ctt gga ggc gct gcc agg gcc ctg gcg cat ggc gtc    784
Val Gly Ala Pro Leu Gly Gly Ala Ala Arg Ala Leu Ala His Gly Val
140                 145                 150                 155 cgg gtt ctg gaa gac ggc gtg aac tat gca aca ggg aac ctt cct ggt    832
Arg Val Leu Glu Asp Gly Val Asn Tyr Ala Thr Gly Asn Leu Pro Gly
                 160                 165                 170 tgc tct ttc tct atc ttc ctt ctg gcc ctg ctc tct tgc ttg act gtg    880
Cys Ser Phe Ser Ile Phe Leu Leu Ala Leu Leu Ser Cys Leu Thr Val
             175                 180                 185 ccc gct tcg gcc tac caa gtg cgc aac tcc acg ggg ctt tac cac gtc    928
Pro Ala Ser Ala Tyr Gln Val Arg Asn Ser Thr Gly Leu Tyr His Val
         190                 195                 200 acc aat gat tgc cct aac tcg agt att gtg tac gag gcg gcc gat gcc    976
Thr Asn Asp Cys Pro Asn Ser Ser Ile Val Tyr Glu Ala Ala Asp Ala
     205                 210                 215 atc ctg cac act ccg ggg tgc gtc cct tgc gtt cgt gag ggc aac gcc   1024
Ile Leu His Thr Pro Gly Cys Val Pro Cys Val Arg Glu Gly Asn Ala
220                 225                 230                 235
```

FIG. 4A

```
tcg agg tgt tgg gtg gcg atg acc cct acg gtg gcc acc agg gat ggc    1072
Ser Arg Cys Trp Val Ala Met Thr Pro Thr Val Ala Thr Arg Asp Gly
            240                 245                 250 aaa ctc ccc gcg acg cag ctt cga cgt cac atc gat ctg ctt gtc ggg    1120
Lys Leu Pro Ala Thr Gln Leu Arg Arg His Ile Asp Leu Leu Val Gly
                255                 260                 265 agc gcc acc ctc tgt tcg gcc ctc tac gtg ggg gac cta tgc ggg tct    1168
Ser Ala Thr Leu Cys Ser Ala Leu Tyr Val Gly Asp Leu Cys Gly Ser
            270                 275                 280 gtc ttt ctt gtc ggc caa ctg ttc acc ttc tct ccc agg cgc cac tgg    1216
Val Phe Leu Val Gly Gln Leu Phe Thr Phe Ser Pro Arg Arg His Trp
        285                 290                 295 acg acg caa ggt tgc aat tgc tct atc tat ccc ggc cat ata acg ggt    1264
Thr Thr Gln Gly Cys Asn Cys Ser Ile Tyr Pro Gly His Ile Thr Gly
300                 305                 310                 315 cac cgc atg gca tgg gat atg atg atg aac tgg tcc cct acg acg gcg    1312
His Arg Met Ala Trp Asp Met Met Met Asn Trp Ser Pro Thr Thr Ala
                320                 325                 330 ttg gta atg gct cag ctg ctc cgg atc cca caa gcc atc ttg gac atg    1360
Leu Val Met Ala Gln Leu Leu Arg Ile Pro Gln Ala Ile Leu Asp Met
            335                 340                 345 atc gct ggt gct cac tgg gga gtc ctg gcg ggc ata gcg tat ttc tcc    1408
Ile Ala Gly Ala His Trp Gly Val Leu Ala Gly Ile Ala Tyr Phe Ser
        350                 355                 360 atg gtg ggg aac tgg gcg aag gtc ctg gta gtg ctg ctg cta ttt gcc    1456
Met Val Gly Asn Trp Ala Lys Val Leu Val Val Leu Leu Leu Phe Ala
365                 370                 375 ggc gtc gac gcg gaa acc cac gtc acc ggg gga agt gcc ggc cac act    1504
Gly Val Asp Ala Glu Thr His Val Thr Gly Gly Ser Ala Gly His Thr
380                 385                 390                 395 gtg tct gga ttt gtt agc ctc ctc gca cca ggc gcc aag cag aac gtc    1552
Val Ser Gly Phe Val Ser Leu Leu Ala Pro Gly Ala Lys Gln Asn Val
                400                 405                 410 cag ctg atc aac acc aac ggc agt tgg cac ctc aat agc acg gcc ctg    1600
Gln Leu Ile Asn Thr Asn Gly Ser Trp His Leu Asn Ser Thr Ala Leu
            415                 420                 425 aac tgc aat gat agc ctc aac acc ggc tgg ttg gca ggg ctt ttc tat    1648
Asn Cys Asn Asp Ser Leu Asn Thr Gly Trp Leu Ala Gly Leu Phe Tyr
        430                 435                 440 cac cac aag ttc aac tct tca ggc tgt cct gag agg cta gcc agc tgc    1696
His His Lys Phe Asn Ser Ser Gly Cys Pro Glu Arg Leu Ala Ser Cys
445                 450                 455 cga ccc ctt acc gat ttt gac cag ggc tgg ggc cct atc agt tat gcc    1744
Arg Pro Leu Thr Asp Phe Asp Gln Gly Trp Gly Pro Ile Ser Tyr Ala
460                 465                 470                 475 aac gga agc ggc ccc gac cag cgc ccc tac tgc tgg cac tac ccc cca    1792
Asn Gly Ser Gly Pro Asp Gln Arg Pro Tyr Cys Trp His Tyr Pro Pro
                480                 485                 490
```

FIG. 4B

```
aaa cct tgc ggt att gtg ccc gcg aag agt gtg tgt ggt ccg gta tat    1840
Lys Pro Cys Gly Ile Val Pro Ala Lys Ser Val Cys Gly Pro Val Tyr
            495                 500                 505 tgc ttc act ccc agc ccc gtg gtg gtg gga acg acc gac agg tcg ggc    1888
Cys Phe Thr Pro Ser Pro Val Val Val Gly Thr Thr Asp Arg Ser Gly
        510                 515                 520 gcg ccc acc tac agc tgg ggt gaa aat gat acg gac gtc ttc gtc ctt    1936
Ala Pro Thr Tyr Ser Trp Gly Glu Asn Asp Thr Asp Val Phe Val Leu
    525                 530                 535 aac aat acc agg cca ccg ctg ggc aat tgg ttc ggt tgt acc tgg atg    1984
Asn Asn Thr Arg Pro Pro Leu Gly Asn Trp Phe Gly Cys Thr Trp Met
540                 545                 550                 555 aac tca act gga ttc acc aaa gtg tgc gga gcg cct cct tgt gtc atc    2032
Asn Ser Thr Gly Phe Thr Lys Val Cys Gly Ala Pro Pro Cys Val Ile
                560                 565                 570 gga ggg gcg ggc aac aac acc ctg cac tgc ccc act gat tgc ttc cgc    2080
Gly Gly Ala Gly Asn Asn Thr Leu His Cys Pro Thr Asp Cys Phe Arg
            575                 580                 585 aag cat ccg gac gcc aca tac tct cgg tgc ggc tcc ggt ccc tgg atc    2128
Lys His Pro Asp Ala Thr Tyr Ser Arg Cys Gly Ser Gly Pro Trp Ile
        590                 595                 600 aca ccc agg tgc ctg gtc gac tac ccg tat agg ctt tgg cat tat cct    2176
Thr Pro Arg Cys Leu Val Asp Tyr Pro Tyr Arg Leu Trp His Tyr Pro
    605                 610                 615 tgt acc atc aac tac acc ata ttt aaa atc agg atg tac gtg gga ggg    2224
Cys Thr Ile Asn Tyr Thr Ile Phe Lys Ile Arg Met Tyr Val Gly Gly
620                 625                 630                 635 gtc gaa cac agg ctg gaa gct gcc tgc aac tgg acg cgg ggc gaa cgt    2272
Val Glu His Arg Leu Glu Ala Ala Cys Asn Trp Thr Arg Gly Glu Arg
                640                 645                 650 tgc gat ctg gaa gac agg gac agg tcc gag ctc agc ccg tta ctg ctg    2320
Cys Asp Leu Glu Asp Arg Asp Arg Ser Glu Leu Ser Pro Leu Leu Leu
            655                 660                 665 acc act aca cag tgg cag gtc ctc ccg tgt tcc ttc aca acc cta cca    2368
Thr Thr Thr Gln Trp Gln Val Leu Pro Cys Ser Phe Thr Thr Leu Pro
        670                 675                 680 gcc ttg tcc acc ggc ctc atc cac ctc cac cag aac att gtg gac gtg    2416
Ala Leu Ser Thr Gly Leu Ile His Leu His Gln Asn Ile Val Asp Val
    685                 690                 695 cag tac ttg tac ggg gtg ggg tca agc atc gcg tcc tgg gcc att aag    2464
Gln Tyr Leu Tyr Gly Val Gly Ser Ser Ile Ala Ser Trp Ala Ile Lys
700                 705                 710                 715 tgg gag tac gtc gtt ctc ctg ttc ctt ctg ctt gca gac gcg cgc gtc    2512
Trp Glu Tyr Val Val Leu Leu Phe Leu Leu Leu Ala Asp Ala Arg Val
                720                 725                 730 tgc tcc tgc ttg tgg atg atg cta ctc ata tcc caa gcg gag gcg gct    2560
Cys Ser Cys Leu Trp Met Met Leu Leu Ile Ser Gln Ala Glu Ala Ala
            735                 740                 745
```

FIG. 4C

| | | | | | | | | | | | | | | | | |
|---|---|---|---|---|---|---|---|---|---|---|---|---|---|---|---|---|
| ttg | gag | aac | ctc | gta | ata | ctt | aat | gca | gca | tcc | ctg | gcc | ggg | acg | cac | 2608 |
| Leu | Glu | Asn | Leu | Val | Ile | Leu | Asn | Ala | Ala | Ser | Leu | Ala | Gly | Thr | His | |
| | | 750 | | | | | 755 | | | | | 760 | | | | |
| ggt | ctt | gta | tcc | ttc | ctc | gtg | ttc | ttc | tgc | ttt | gca | tgg | tat | ttg | aag | 2656 |
| Gly | Leu | Val | Ser | Phe | Leu | Val | Phe | Phe | Cys | Phe | Ala | Trp | Tyr | Leu | Lys | |
| | 765 | | | | | 770 | | | | | 775 | | | | | |
| ggt | aag | tgg | gtg | ccc | gga | gcg | gtc | tac | acc | ttc | tac | ggg | atg | tgg | cct | 2704 |
| Gly | Lys | Trp | Val | Pro | Gly | Ala | Val | Tyr | Thr | Phe | Tyr | Gly | Met | Trp | Pro | |
| 780 | | | | | 785 | | | | | 790 | | | | | 795 | |
| ctc | ctc | ctg | ctc | ctg | ttg | gcg | ttg | ccc | cag | cgg | gcg | tac | gcg | ctg | gac | 2752 |
| Leu | Leu | Leu | Leu | Leu | Leu | Ala | Leu | Pro | Gln | Arg | Ala | Tyr | Ala | Leu | Asp | |
| | | | | 800 | | | | | 805 | | | | | 810 | | |
| acg | gag | gtg | gcc | gcg | tcg | tgt | ggc | ggt | gtt | gtt | ctc | gtc | ggg | ttg | atg | 2800 |
| Thr | Glu | Val | Ala | Ala | Ser | Cys | Gly | Gly | Val | Val | Leu | Val | Gly | Leu | Met | |
| | | | | 815 | | | | | 820 | | | | | 825 | | |
| gcg | ctg | act | ctg | tca | cca | tat | tac | aag | cgc | tat | atc | agc | tgg | tgc | ttg | 2848 |
| Ala | Leu | Thr | Leu | Ser | Pro | Tyr | Tyr | Lys | Arg | Tyr | Ile | Ser | Trp | Cys | Leu | |
| | | | 830 | | | | | 835 | | | | | 840 | | | |
| tgg | tgg | ctt | cag | tat | ttt | ctg | acc | aga | gtg | gaa | gcg | caa | ctg | cac | gtg | 2896 |
| Trp | Trp | Leu | Gln | Tyr | Phe | Leu | Thr | Arg | Val | Glu | Ala | Gln | Leu | His | Val | |
| | 845 | | | | | 850 | | | | | 855 | | | | | |
| tgg | att | ccc | ccc | ctc | aac | gtc | cga | ggg | ggg | cgc | gac | gcc | gtc | atc | tta | 2944 |
| Trp | Ile | Pro | Pro | Leu | Asn | Val | Arg | Gly | Gly | Arg | Asp | Ala | Val | Ile | Leu | |
| 860 | | | | | 865 | | | | | 870 | | | | | 875 | |
| ctc | atg | tgt | gct | gta | cac | ccg | act | ctg | gta | ttt | gac | atc | acc | aaa | ttg | 2992 |
| Leu | Met | Cys | Ala | Val | His | Pro | Thr | Leu | Val | Phe | Asp | Ile | Thr | Lys | Leu | |
| | | | | 880 | | | | | 885 | | | | | 890 | | |
| ctg | ctg | gcc | gtc | ttc | gga | ccc | ctt | tgg | att | ctt | caa | gcc | agt | ttg | ctt | 3040 |
| Leu | Leu | Ala | Val | Phe | Gly | Pro | Leu | Trp | Ile | Leu | Gln | Ala | Ser | Leu | Leu | |
| | | | 895 | | | | | 900 | | | | | 905 | | | |
| aaa | gta | ccc | tac | ttt | gtg | cgc | gtc | caa | ggc | ctt | ctc | cgg | ttc | tgc | gcg | 3088 |
| Lys | Val | Pro | Tyr | Phe | Val | Arg | Val | Gln | Gly | Leu | Leu | Arg | Phe | Cys | Ala | |
| | | 910 | | | | | 915 | | | | | 920 | | | | |
| tta | gcg | cgg | aag | atg | atc | gga | ggc | cat | tac | gtg | caa | atg | gtc | atc | att | 3136 |
| Leu | Ala | Arg | Lys | Met | Ile | Gly | Gly | His | Tyr | Val | Gln | Met | Val | Ile | Ile | |
| | 925 | | | | | 930 | | | | | 935 | | | | | |
| aag | tta | ggg | gcg | ctt | act | ggc | acc | tat | gtt | tat | aac | cat | ctc | act | cct | 3184 |
| Lys | Leu | Gly | Ala | Leu | Thr | Gly | Thr | Tyr | Val | Tyr | Asn | His | Leu | Thr | Pro | |
| 940 | | | | | 945 | | | | | 950 | | | | | 955 | |
| ctt | cgg | gac | tgg | gcg | cac | aac | ggc | ttg | cga | gat | ctg | gcc | gtg | gct | gta | 3232 |
| Leu | Arg | Asp | Trp | Ala | His | Asn | Gly | Leu | Arg | Asp | Leu | Ala | Val | Ala | Val | |
| | | | | 960 | | | | | 965 | | | | | 970 | | |
| gag | cca | gtc | gtc | ttc | tcc | caa | atg | gag | acc | aag | ctc | atc | acg | tgg | ggg | 3280 |
| Glu | Pro | Val | Val | Phe | Ser | Gln | Met | Glu | Thr | Lys | Leu | Ile | Thr | Trp | Gly | |
| | | | 975 | | | | | 980 | | | | | 985 | | | |
| gca | gat | acc | gcc | gcg | tgc | ggt | gac | atc | atc | aac | ggc | ttg | cct | gtt | tcc | 3328 |
| Ala | Asp | Thr | Ala | Ala | Cys | Gly | Asp | Ile | Ile | Asn | Gly | Leu | Pro | Val | Ser | |
| | | 990 | | | | | 995 | | | | | 1000 | | | | |

FIG. 4D

```
gcc cgc agg ggc cgg gag ata ctg ctc ggg cca gcc gat gga atg gtc   3376
Ala Arg Arg Gly Arg Glu Ile Leu Leu Gly Pro Ala Asp Gly Met Val
    1005                1010                1015 tcc aag ggg tgg agg ttg ctg gcg ccc atc acg gcg tac gcc cag cag   3424
Ser Lys Gly Trp Arg Leu Leu Ala Pro Ile Thr Ala Tyr Ala Gln Gln
1020                1025                1030                1035 aca agg ggc ctc cta ggg tgc ata atc acc agc cta act ggc cgg gac   3472
Thr Arg Gly Leu Leu Gly Cys Ile Ile Thr Ser Leu Thr Gly Arg Asp
                1040                1045                1050 aaa aac caa gtg gag ggt gag gtc cag att gtg tca act gct gcc caa   3520
Lys Asn Gln Val Glu Gly Glu Val Gln Ile Val Ser Thr Ala Ala Gln
            1055                1060                1065 acc ttc ctg gca acg tgc atc aat ggg gtg tgc tgg act gtc tac cac   3568
Thr Phe Leu Ala Thr Cys Ile Asn Gly Val Cys Trp Thr Val Tyr His
            1070                1075                1080 ggg gcc gga acg agg acc atc gcg tca ccc aag ggt cct gtc atc cag   3616
Gly Ala Gly Thr Arg Thr Ile Ala Ser Pro Lys Gly Pro Val Ile Gln
            1085                1090                1095 atg tat acc aat gta gac caa gac ctt gtg ggc tgg ccc gct ccg caa   3664
Met Tyr Thr Asn Val Asp Gln Asp Leu Val Gly Trp Pro Ala Pro Gln
1100                1105                1110                1115 ggt agc cgc tca ttg aca ccc tgc act tgc ggc tcc tcg gac ctt tac   3712
Gly Ser Arg Ser Leu Thr Pro Cys Thr Cys Gly Ser Ser Asp Leu Tyr
                1120                1125                1130 ctg gtc acg agg cac gcc gat gtc att ccc gtg cgc cgg cgg ggt gat   3760
Leu Val Thr Arg His Ala Asp Val Ile Pro Val Arg Arg Arg Gly Asp
            1135                1140                1145 agc agg ggc agc ctg ctg tcg ccc cgg ccc att tcc tac ttg aaa ggc   3808
Ser Arg Gly Ser Leu Leu Ser Pro Arg Pro Ile Ser Tyr Leu Lys Gly
            1150                1155                1160 tcc tcg ggg ggt ccg ctg ttg tgc ccc gcg ggg cac gcc gtg ggc ata   3856
Ser Ser Gly Gly Pro Leu Leu Cys Pro Ala Gly His Ala Val Gly Ile
            1165                1170                1175 ttt agg gcc gcg gtg tgc acc cgt gga gtg gct aag gcg gtg gac ttt   3904
Phe Arg Ala Ala Val Cys Thr Arg Gly Val Ala Lys Ala Val Asp Phe
1180                1185                1190                1195 atc cct gtg gag aac cta gag aca acc atg agg tcc ccg gtg ttc acg   3952
Ile Pro Val Glu Asn Leu Glu Thr Thr Met Arg Ser Pro Val Phe Thr
                1200                1205                1210 gat aac tcc tct cca cca gta gtg ccc cag agc ttc cag gtg gct cac   4000
Asp Asn Ser Ser Pro Pro Val Val Pro Gln Ser Phe Gln Val Ala His
            1215                1220                1225 ctc cat gct ccc aca ggc agc ggc aaa agc acc aag gtc ccg gct gca   4048
Leu His Ala Pro Thr Gly Ser Gly Lys Ser Thr Lys Val Pro Ala Ala
            1230                1235                1240 tat gca gct cag ggc tat aag gtg cta gta ctc aac ccc tct gtt gct   4096
Tyr Ala Ala Gln Gly Tyr Lys Val Leu Val Leu Asn Pro Ser Val Ala
            1245                1250                1255
```

FIG. 4E

```
gca aca ctg ggc ttt ggt gct tac atg tcc aag gct cat ggg atc gat    4144
Ala Thr Leu Gly Phe Gly Ala Tyr Met Ser Lys Ala His Gly Ile Asp
1260                1265                1270                1275 cct aac atc agg acc ggg gtg aga aca att acc act ggc agc ccc atc    4192
Pro Asn Ile Arg Thr Gly Val Arg Thr Ile Thr Thr Gly Ser Pro Ile
                1280                1285                1290 acg tac tcc acc tac ggc aag ttc ctt gcc gac ggc ggg tgc tcg ggg    4240
Thr Tyr Ser Thr Tyr Gly Lys Phe Leu Ala Asp Gly Gly Cys Ser Gly
            1295                1300                1305 ggc gct tat gac ata ata att tgt gac gag tgc cac tcc acg gat gcc    4288
Gly Ala Tyr Asp Ile Ile Ile Cys Asp Glu Cys His Ser Thr Asp Ala
        1310                1315                1320 aca tcc atc ttg ggc atc ggc act gtc ctt gac caa gca gag act gcg    4336
Thr Ser Ile Leu Gly Ile Gly Thr Val Leu Asp Gln Ala Glu Thr Ala
    1325                1330                1335 ggg gcg aga ctg gtt gtg ctc gcc acc gcc acc cct ccg ggc tcc gtc    4384
Gly Ala Arg Leu Val Val Leu Ala Thr Ala Thr Pro Pro Gly Ser Val
1340                1345                1350                1355 act gtg ccc cat ccc aac atc gag gag gtt gct ctg tcc acc acc gga    4432
Thr Val Pro His Pro Asn Ile Glu Glu Val Ala Leu Ser Thr Thr Gly
                1360                1365                1370 gag atc cct ttt tac ggc aag gct atc ccc ctc gaa gta atc aag ggg    4480
Glu Ile Pro Phe Tyr Gly Lys Ala Ile Pro Leu Glu Val Ile Lys Gly
            1375                1380                1385 ggg aga cat ctc atc ttc tgt cat tca aag aag aag tgc gac gaa ctc    4528
Gly Arg His Leu Ile Phe Cys His Ser Lys Lys Lys Cys Asp Glu Leu
        1390                1395                1400 gcc gca aag ctg gtc gca ttg ggc atc aat gcc gtg gcc tac tac cgc    4576
Ala Ala Lys Leu Val Ala Leu Gly Ile Asn Ala Val Ala Tyr Tyr Arg
    1405                1410                1415 ggt ctt gac gtg tcc gtc atc ccg acc agc ggc gat gtt gtc gtc gtg    4624
Gly Leu Asp Val Ser Val Ile Pro Thr Ser Gly Asp Val Val Val Val
1420                1425                1430                1435 gca acc gat gcc ctc atg acc ggc tat acc ggc gac ttc gac tcg gtg    4672
Ala Thr Asp Ala Leu Met Thr Gly Tyr Thr Gly Asp Phe Asp Ser Val
                1440                1445                1450 ata gac tgc aat acg tgt gtc acc cag aca gtc gat ttc agc ctt gac    4720
Ile Asp Cys Asn Thr Cys Val Thr Gln Thr Val Asp Phe Ser Leu Asp
            1455                1460                1465 cct acc ttc acc att gag aca atc acg ctc ccc cag gat gct gtc tcc    4768
Pro Thr Phe Thr Ile Glu Thr Ile Thr Leu Pro Gln Asp Ala Val Ser
        1470                1475                1480 cgc act caa cgt cgg ggc agg act ggc agg ggg aag cca ggc atc tac    4816
Arg Thr Gln Arg Arg Gly Arg Thr Gly Arg Gly Lys Pro Gly Ile Tyr
    1485                1490                1495 aga ttt gtg gca ccg ggg gag cgc ccc tcc ggc atg ttc gac tcg tcc    4864
Arg Phe Val Ala Pro Gly Glu Arg Pro Ser Gly Met Phe Asp Ser Ser
1500                1505                1510                1515
```

FIG. 4F

```
gtc ctc tgt gag tgc tat gac gca ggc tgt gct tgg tat gag ctc acg      4912
Val Leu Cys Glu Cys Tyr Asp Ala Gly Cys Ala Trp Tyr Glu Leu Thr
            1520                1525                1530 ccc gcc gag act aca gtt agg cta cga gcg tac atg aac acc ccg ggg      4960
Pro Ala Glu Thr Thr Val Arg Leu Arg Ala Tyr Met Asn Thr Pro Gly
        1535                1540                1545 ctt ccc gtg tgc cag gac cat ctt gaa ttt tgg gag ggc gtc ttt aca      5008
Leu Pro Val Cys Gln Asp His Leu Glu Phe Trp Glu Gly Val Phe Thr
    1550                1555                1560 ggc ctc act cat ata gat gcc cac ttt cta tcc cag aca aag cag agt      5056
Gly Leu Thr His Ile Asp Ala His Phe Leu Ser Gln Thr Lys Gln Ser
1565                1570                1575 ggg gag aac ctt cct tac ctg gta gcg tac caa gcc acc gtg tgc gct      5104
Gly Glu Asn Leu Pro Tyr Leu Val Ala Tyr Gln Ala Thr Val Cys Ala
1580                1585                1590                1595 agg gct caa gcc cct ccc cca tcg tgg gac cag atg tgg aag tgt ttg      5152
Arg Ala Gln Ala Pro Pro Pro Ser Trp Asp Gln Met Trp Lys Cys Leu
            1600                1605                1610 att cgc ctc aag ccc acc ctc cat ggg cca aca ccc cta tac aga           5200
Ile Arg Leu Lys Pro Thr Leu His Gly Pro Thr Pro Leu Leu Tyr Arg
        1615                1620                1625 ctg ggc gct gtt cag aat gaa atc acc ctg acg cac cca gtc acc aaa      5248
Leu Gly Ala Val Gln Asn Glu Ile Thr Leu Thr His Pro Val Thr Lys
    1630                1635                1640 tac atc atg aca tgc atg tcg gcc gac ctg gag gtc gtc acg agc acc      5296
Tyr Ile Met Thr Cys Met Ser Ala Asp Leu Glu Val Val Thr Ser Thr
1645                1650                1655 tgg gtg ctc gtt ggc ggc gtc ctg gct gct ttg gcc gcg tat tgc ctg      5344
Trp Val Leu Val Gly Gly Val Leu Ala Ala Leu Ala Ala Tyr Cys Leu
1660                1665                1670                1675 tca aca ggc tgc gtg gtc ata gtg ggc agg gtc gtc ttg tcc ggg aag      5392
Ser Thr Gly Cys Val Val Ile Val Gly Arg Val Val Leu Ser Gly Lys
            1680                1685                1690 ccg gca atc ata cct gac agg gaa gtc ctc tac cga gag ttc gat gag      5440
Pro Ala Ile Ile Pro Asp Arg Glu Val Leu Tyr Arg Glu Phe Asp Glu
        1695                1700                1705 atg gaa gag tgc tct cag cac tta ccg tac atc gag caa ggg atg atg      5488
Met Glu Glu Cys Ser Gln His Leu Pro Tyr Ile Glu Gln Gly Met Met
    1710                1715                1720 ctc gcc gag cag ttc aag cag aag gcc ctc ggc ctc ctg cag acc gcg      5536
Leu Ala Glu Gln Phe Lys Gln Lys Ala Leu Gly Leu Leu Gln Thr Ala
1725                1730                1735 tcc cgt cag gca gag gtt atc gcc cct gct gtc cag acc aac tgg caa      5584
Ser Arg Gln Ala Glu Val Ile Ala Pro Ala Val Gln Thr Asn Trp Gln
1740                1745                1750                1755 aaa ctc gag acc ttc tgg gcg aag cat atg tgg aac ttc atc agt ggg      5632
Lys Leu Glu Thr Phe Trp Ala Lys His Met Trp Asn Phe Ile Ser Gly
            1760                1765                1770
```

FIG. 4G

```
ata caa tac ttg gcg ggc ttg tca acg ctg cct ggt aac ccc gcc att     5680
Ile Gln Tyr Leu Ala Gly Leu Ser Thr Leu Pro Gly Asn Pro Ala Ile
        1775                1780                1785 gct tca ttg atg gct ttt aca gct gct gtc acc agc cca cta acc act     5728
Ala Ser Leu Met Ala Phe Thr Ala Ala Val Thr Ser Pro Leu Thr Thr
    1790                1795                1800 agc caa acc ctc ctc ttc aac ata ttg ggg ggg tgg gtg gct gcc cag     5776
Ser Gln Thr Leu Leu Phe Asn Ile Leu Gly Gly Trp Val Ala Ala Gln
    1805                1810                1815 ctc gcc gcc ccc ggt gcc gct act gcc ttt gtg ggc gct ggc tta gct     5824
Leu Ala Ala Pro Gly Ala Ala Thr Ala Phe Val Gly Ala Gly Leu Ala
1820            1825                1830                1835 ggc gcc gcc atc ggc agt gtt gga ctg ggg aag gtc ctc ata gac atc     5872
Gly Ala Ala Ile Gly Ser Val Gly Leu Gly Lys Val Leu Ile Asp Ile
                1840                1845                1850 ctt gca ggg tat ggc gcg ggc gtg gcg gga gct ctt gtg gca ttc aag     5920
Leu Ala Gly Tyr Gly Ala Gly Val Ala Gly Ala Leu Val Ala Phe Lys
        1855                1860                1865 atc atg agc ggt gag gtc ccc tcc acg gag gac ctg gtc aat cta ctg     5968
Ile Met Ser Gly Glu Val Pro Ser Thr Glu Asp Leu Val Asn Leu Leu
    1870                1875                1880 ccc gcc atc ctc tcg ccc gga gcc ctc gta gtc ggc gtg gtc tgt gca     6016
Pro Ala Ile Leu Ser Pro Gly Ala Leu Val Val Gly Val Val Cys Ala
    1885                1890                1895 gca ata ctg cgc cgg cac gtt ggc ccg ggc gag ggg gca gtg cag tgg     6064
Ala Ile Leu Arg Arg His Val Gly Pro Gly Glu Gly Ala Val Gln Trp
1900            1905                1910                1915 atg aac cgg ctg ata gcc ttc gcc tcc cgg ggg aac cat gtt tcc ccc     6112
Met Asn Arg Leu Ile Ala Phe Ala Ser Arg Gly Asn His Val Ser Pro
                1920                1925                1930 acg cac tac gtg ccg gag agc gat gca gct gcc cgc gtc act gcc ata     6160
Thr His Tyr Val Pro Glu Ser Asp Ala Ala Ala Arg Val Thr Ala Ile
        1935                1940                1945 ctc agc agc ctc act gta acc cag ctc ctg agg cga ctg cac cag tgg     6208
Leu Ser Ser Leu Thr Val Thr Gln Leu Leu Arg Arg Leu His Gln Trp
    1950                1955                1960 ata agc tcg gag tgt acc act cca tgc tcc ggt tcc tgg cta agg gac     6256
Ile Ser Ser Glu Cys Thr Thr Pro Cys Ser Gly Ser Trp Leu Arg Asp
    1965                1970                1975 atc tgg gac tgg ata tgc gag gtg ttg agc gac ttt aag acc tgg cta     6304
Ile Trp Asp Trp Ile Cys Glu Val Leu Ser Asp Phe Lys Thr Trp Leu
1980            1985                1990                1995 aaa gct aag ctc atg cca cag ctg cct ggg atc ccc ttt gtg tcc tgc     6352
Lys Ala Lys Leu Met Pro Gln Leu Pro Gly Ile Pro Phe Val Ser Cys
                2000                2005                2010 cag cgc ggg tat aag ggg gtc tgg cga gtg gac ggc atc atg cac act     6400
Gln Arg Gly Tyr Lys Gly Val Trp Arg Val Asp Gly Ile Met His Thr
        2015                2020                2025
```

FIG. 4H

```
cgc tgc cac tgt gga gct gag atc act gga cat gtc aaa aac ggg acg    6448
Arg Cys His Cys Gly Ala Glu Ile Thr Gly His Val Lys Asn Gly Thr
        2030                2035                2040 atg agg atc gtc ggt cct agg acc tgc agg aac atg tgg agt ggg acc    6496
Met Arg Ile Val Gly Pro Arg Thr Cys Arg Asn Met Trp Ser Gly Thr
2045                2050                2055 ttc ccc att aat gcc tac acc acg ggc ccc tgt acc ccc ctt cct gcg    6544
Phe Pro Ile Asn Ala Tyr Thr Thr Gly Pro Cys Thr Pro Leu Pro Ala
2060                2065                2070                2075 ccg aac tac acg ttc gcg cta tgg agg gtg tct gca gag gaa tat gtg    6592
Pro Asn Tyr Thr Phe Ala Leu Trp Arg Val Ser Ala Glu Glu Tyr Val
            2080                2085                2090 gag ata agg cag gtg ggg gac ttc cac tac gtg acg ggt atg act act    6640
Glu Ile Arg Gln Val Gly Asp Phe His Tyr Val Thr Gly Met Thr Thr
        2095                2100                2105 gac aat ctc aaa tgc ccg tgc cag gtc cca tcg ccc gaa ttt ttc aca    6688
Asp Asn Leu Lys Cys Pro Cys Gln Val Pro Ser Pro Glu Phe Phe Thr
        2110                2115                2120 gaa ttg gac ggg gtg cgc cta cat agg ttt gcg ccc ccc tgc aag ccc    6736
Glu Leu Asp Gly Val Arg Leu His Arg Phe Ala Pro Pro Cys Lys Pro
2125                2130                2135 ttg ctg cgg gag gag gta tca ttc aga gta gga ctc cac gaa tac ccg    6784
Leu Leu Arg Glu Glu Val Ser Phe Arg Val Gly Leu His Glu Tyr Pro
2140                2145                2150                2155 gta ggg tcg caa tta cct tgc gag ccc gaa ccg gac gtg gcc gtg ttg    6832
Val Gly Ser Gln Leu Pro Cys Glu Pro Glu Pro Asp Val Ala Val Leu
            2160                2165                2170 acg tcc atg ctc act gat ccc tcc cat ata aca gca gag gcg gcc ggg    6880
Thr Ser Met Leu Thr Asp Pro Ser His Ile Thr Ala Glu Ala Ala Gly
            2175                2180                2185 cga agg ttg gcg agg gga tca ccc ccc tct gtg gcc agc tcc tcg gct    6928
Arg Arg Leu Ala Arg Gly Ser Pro Pro Ser Val Ala Ser Ser Ser Ala
        2190                2195                2200 agc cag cta tcc gct cca tct ctc aag gca act tgc acc gct aac cat    6976
Ser Gln Leu Ser Ala Pro Ser Leu Lys Ala Thr Cys Thr Ala Asn His
        2205                2210                2215 gac tcc cct gat gct gag ctc ata gag gcc aac ctc cta tgg agg cag    7024
Asp Ser Pro Asp Ala Glu Leu Ile Glu Ala Asn Leu Leu Trp Arg Gln
2220                2225                2230                2235 gag atg ggc ggc aac atc acc agg gtt gag tca gaa aac aaa gtg gtg    7072
Glu Met Gly Gly Asn Ile Thr Arg Val Glu Ser Glu Asn Lys Val Val
                2240                2245                2250 att ctg gac tcc ttc gat ccg ctt gtg gcg gag gag gac gag cgg gag    7120
Ile Leu Asp Ser Phe Asp Pro Leu Val Ala Glu Glu Asp Glu Arg Glu
            2255                2260                2265 atc tcc gta ccc gca gaa atc ctg cgg aag tct cgg aga ttc gcc cag    7168
Ile Ser Val Pro Ala Glu Ile Leu Arg Lys Ser Arg Arg Phe Ala Gln
        2270                2275                2280
```

FIG. 4I

```
gcc ctg ccc gtt tgg gcg cgg ccg gac tat aac ccc ccg cta gtg gag    7216
Ala Leu Pro Val Trp Ala Arg Pro Asp Tyr Asn Pro Pro Leu Val Glu
2285                2290                2295 acg tgg aaa aag ccc gac tac gaa cca cct gtg gtc cat ggc tgt ccg    7264
Thr Trp Lys Lys Pro Asp Tyr Glu Pro Pro Val Val His Gly Cys Pro
2300                2305                2310                2315 ctt cca cct cca aag tcc cct cct gtg cct ccg cct cgg aag aag cgg    7312
Leu Pro Pro Pro Lys Ser Pro Pro Val Pro Pro Pro Arg Lys Lys Arg
            2320                2325                2330 acg gtg gtc ctc act gaa tca acc cta tct act gcc ttg gcc gag ctc    7360
Thr Val Val Leu Thr Glu Ser Thr Leu Ser Thr Ala Leu Ala Glu Leu
2335                2340                2345 gcc acc aga agc ttt ggc agc tcc tca act tcc ggc att acg ggc gac    7408
Ala Thr Arg Ser Phe Gly Ser Ser Ser Thr Ser Gly Ile Thr Gly Asp
        2350                2355                2360 aat acg aca aca tcc tct gag ccc gcc cct tct ggc tgc ccc ccc gac    7456
Asn Thr Thr Thr Ser Ser Glu Pro Ala Pro Ser Gly Cys Pro Pro Asp
2365                2370                2375 tcc gac gct gag tcc tat tcc tcc atg ccc ccc ctg gag ggg gag cct    7504
Ser Asp Ala Glu Ser Tyr Ser Ser Met Pro Pro Leu Glu Gly Glu Pro
2380                2385                2390                2395 ggg gat ccg gat ctt agc gac ggg tca tgg tca acg gtc agt agt gag    7552
Gly Asp Pro Asp Leu Ser Asp Gly Ser Trp Ser Thr Val Ser Ser Glu
            2400                2405                2410 gcc aac gcg gag gat gtc gtg tgc tgc tca atg tct tac tct tgg aca    7600
Ala Asn Ala Glu Asp Val Val Cys Cys Ser Met Ser Tyr Ser Trp Thr
        2415                2420                2425 ggc gca ctc gtc acc ccg tgc gcc gcg gaa gaa cag aaa ctg ccc atc    7648
Gly Ala Leu Val Thr Pro Cys Ala Ala Glu Glu Gln Lys Leu Pro Ile
        2430                2435                2440 aat gca cta agc aac tcg ttg cta cgt cac cac aat ttg gtg tat tcc    7696
Asn Ala Leu Ser Asn Ser Leu Leu Arg His His Asn Leu Val Tyr Ser
2445                2450                2455 acc acc tca cgc agt gct tgc caa agg cag aag aaa gtc aca ttt gac    7744
Thr Thr Ser Arg Ser Ala Cys Gln Arg Gln Lys Lys Val Thr Phe Asp
2460                2465                2470                2475 aga ctg caa gtt ctg gac agc cat tac cag gac gta ctc aag gag gtt    7792
Arg Leu Gln Val Leu Asp Ser His Tyr Gln Asp Val Leu Lys Glu Val
            2480                2485                2490 aaa gca gcg gcg tca aaa gtg aag gct aac ttg cta tcc gta gag gaa    7840
Lys Ala Ala Ala Ser Lys Val Lys Ala Asn Leu Leu Ser Val Glu Glu
        2495                2500                2505 gct tgc agc ctg acg ccc cca cac tca gcc aaa tcc aag ttt ggt tat    7888
Ala Cys Ser Leu Thr Pro Pro His Ser Ala Lys Ser Lys Phe Gly Tyr
        2510                2515                2520 ggg gca aaa gac gtc cgt tgc cat gcc aga aag gcc gta acc cac atc    7936
Gly Ala Lys Asp Val Arg Cys His Ala Arg Lys Ala Val Thr His Ile
2525                2530                2535
```

FIG. 4J

```
aac tcc gtg tgg aaa gac ctt ctg gaa gac aat gta aca cca ata gac       7984
Asn Ser Val Trp Lys Asp Leu Leu Glu Asp Asn Val Thr Pro Ile Asp
2540            2545                2550                2555 act acc atc atg gct aag aac gag gtt ttc tgc gtt cag cct gag aag       8032
Thr Thr Ile Met Ala Lys Asn Glu Val Phe Cys Val Gln Pro Glu Lys
        2560                2565                2570 ggg ggt cgt aag cca gct cgt ctc atc gtg ttc ccc gat ctg ggc gtg       8080
Gly Gly Arg Lys Pro Ala Arg Leu Ile Val Phe Pro Asp Leu Gly Val
            2575                2580                2585 cgc gtg tgc gaa aag atg gct ttg tac gac gtg gtt aca aag ctc ccc       8128
Arg Val Cys Glu Lys Met Ala Leu Tyr Asp Val Val Thr Lys Leu Pro
                2590                2595                2600 ttg gcc gtg atg gga agc tcc tac gga ttc caa tac tca cca gga cag       8176
Leu Ala Val Met Gly Ser Ser Tyr Gly Phe Gln Tyr Ser Pro Gly Gln
            2605                2610                2615 cgg gtt gaa ttc ctc gtg caa gcg tgg aag tcc aag aaa acc cca atg       8224
Arg Val Glu Phe Leu Val Gln Ala Trp Lys Ser Lys Lys Thr Pro Met
2620            2625                2630                2635 ggg ttc tcg tat gat acc cgc tgc ttt gac tcc aca gtc act gag agc       8272
Gly Phe Ser Tyr Asp Thr Arg Cys Phe Asp Ser Thr Val Thr Glu Ser
        2640                2645                2650 gac atc cgt acg gag gag gca atc tac caa tgt tgt gac ctc gac ccc       8320
Asp Ile Arg Thr Glu Glu Ala Ile Tyr Gln Cys Cys Asp Leu Asp Pro
            2655                2660                2665 caa gcc cgc gtg gcc atc aag tcc ctc acc gag agg ctt tat gtt ggg       8368
Gln Ala Arg Val Ala Ile Lys Ser Leu Thr Glu Arg Leu Tyr Val Gly
                2670                2675                2680 ggc cct ctt acc aat tca agg ggg gag aac tgc ggc tat cgc agg tgc       8416
Gly Pro Leu Thr Asn Ser Arg Gly Glu Asn Cys Gly Tyr Arg Arg Cys
            2685                2690                2695 cgc gcg agc ggc gta ctg aca act agc tgt ggt aac acc ctc act tgc       8464
Arg Ala Ser Gly Val Leu Thr Thr Ser Cys Gly Asn Thr Leu Thr Cys
2700            2705                2710                2715 tac atc aag gcc cgg gca gcc tgt cga gcc gca ggg ctc cag gac tgc       8512
Tyr Ile Lys Ala Arg Ala Ala Cys Arg Ala Ala Gly Leu Gln Asp Cys
        2720                2725                2730 acc atg ctc gtg tgt ggc gac gac tta gtc gtt atc tgt gaa agc gcg       8560
Thr Met Leu Val Cys Gly Asp Asp Leu Val Val Ile Cys Glu Ser Ala
            2735                2740                2745 ggg gtc cag gag gac gcg gcg agc ctg aga gcc ttc acg gag gct atg       8608
Gly Val Gln Glu Asp Ala Ala Ser Leu Arg Ala Phe Thr Glu Ala Met
                2750                2755                2760 acc agg tac tcc gcc ccc cct ggg gac ccc cca caa cca gaa tac gac       8656
Thr Arg Tyr Ser Ala Pro Pro Gly Asp Pro Pro Gln Pro Glu Tyr Asp
            2765                2770                2775 ttg gag ctc ata aca tca tgc tcc tcc aac gtg tca gtc gcc cac gac       8704
Leu Glu Leu Ile Thr Ser Cys Ser Ser Asn Val Ser Val Ala His Asp
2780            2785                2790                2795
```

FIG. 4K

```
ggc gct gga aag agg gtc tac tac ctc acc cgt gac cct aca acc ccc    8752
Gly Ala Gly Lys Arg Val Tyr Tyr Leu Thr Arg Asp Pro Thr Thr Pro
            2800            2805                2810 ctc gcg aga gct gcg tgg gag aca gca aga cac act cca gtc aat tcc    8800
Leu Ala Arg Ala Ala Trp Glu Thr Ala Arg His Thr Pro Val Asn Ser
        2815                2820                2825 tgg cta ggc aac ata atc atg ttt gcc ccc aca ctg tgg gcg agg atg    8848
Trp Leu Gly Asn Ile Ile Met Phe Ala Pro Thr Leu Trp Ala Arg Met
        2830                2835                2840 ata ctg atg acc cat ttc ttt agc gtc ctt ata gcc agg gac cag ctt    8896
Ile Leu Met Thr His Phe Phe Ser Val Leu Ile Ala Arg Asp Gln Leu
    2845                2850                2855 gaa cag gcc ctc gat tgc gag atc tac ggg gcc tgc tac tcc ata gaa    8944
Glu Gln Ala Leu Asp Cys Glu Ile Tyr Gly Ala Cys Tyr Ser Ile Glu
2860                2865                2870                2875 cca ctt gat cta cct cca atc att caa aga ctc cat ggc ctc agc gca    8992
Pro Leu Asp Leu Pro Pro Ile Ile Gln Arg Leu His Gly Leu Ser Ala
            2880                2885                2890 ttt tca ctc cac agt tac tct cca ggt gaa att aat agg gtg gcc gca    9040
Phe Ser Leu His Ser Tyr Ser Pro Gly Glu Ile Asn Arg Val Ala Ala
        2895                2900                2905 tgc ctc aga aaa ctt ggg gta ccg ccc ttg cga gct tgg aga cac cgg    9088
Cys Leu Arg Lys Leu Gly Val Pro Pro Leu Arg Ala Trp Arg His Arg
        2910                2915                2920 gcc cgg agc gtc cgc gct agg ctt ctg gcc aga gga ggc agg gct gcc    9136
Ala Arg Ser Val Arg Ala Arg Leu Leu Ala Arg Gly Gly Arg Ala Ala
        2925                2930                2935 ata tgt ggc aag tac ctc ttc aac tgg gca gta aga aca aag ctc aaa    9184
Ile Cys Gly Lys Tyr Leu Phe Asn Trp Ala Val Arg Thr Lys Leu Lys
2940                2945                2950                2955 ctc act cca ata gcg gcc gct ggc cag ctg gac ttg tcc ggc tgg ttc    9232
Leu Thr Pro Ile Ala Ala Ala Gly Gln Leu Asp Leu Ser Gly Trp Phe
            2960                2965                2970 acg gct ggc tac agc ggg gga gac att tat cac agc gtg tct cat gcc    9280
Thr Ala Gly Tyr Ser Gly Gly Asp Ile Tyr His Ser Val Ser His Ala
        2975                2980                2985 cgg ccc cgc tgg atc tgg ttt tgc cta ctc ctg ctt gct gca ggg gta    9328
Arg Pro Arg Trp Ile Trp Phe Cys Leu Leu Leu Leu Ala Ala Gly Val
        2990                2995                3000 ggc atc tac ctc ctc ccc aac cga tgaaggttgg ggtaaacact ccggcct      9379
Gly Ile Tyr Leu Leu Pro Asn Arg
3005                3010
```

FIG. 4L

SEQUENCE LISTING

<160> NUMBER OF SEQ ID NOS: 2

<210> SEQ ID NO 1
<211> LENGTH: 9379
<212> TYPE: DNA
<213> ORGANISM: Virus
<220> FEATURE:
<221> NAME/KEY: CDS
<222> LOCATION: (320)...(9352)

<400> SEQUENCE: 1

```
cactccacca tgaatcactc ccctgtgagg aactactgtc ttcacgcaga aagcgtctag     60
ccatggcgtt agtatgagtg tcgtgcagcc tccaggaccc cccctcccgg gagagccata    120
gtggtctgcg aaccggtga gtacaccgga attgccagga cgaccgggtc ctttcttgga    180
tcaacccgct caatgcctgg agatttgggc gtgcccccgc aagactgcta gccgagtagt    240
gttgggtcgc gaaaggcctt gtggtactgc ctgatagggt gcttgcgagt gccccgggag    300
gtctcgtaga ccgtgcacc atg agc acg aat cct aaa cct caa aaa aaa aac    352
                    Met Ser Thr Asn Pro Lys Pro Gln Lys Lys Asn
                     1               5                  10 aaa cgt aac acc aac cgt cgc cca cag gac gtc aag ttc ccg ggt ggc    400
Lys Arg Asn Thr Asn Arg Arg Pro Gln Asp Val Lys Phe Pro Gly Gly
            15                  20                  25 ggt cag atc gtt ggt gga gtt tac ttg ttg ccg cgc agg ggc cct aga    448
Gly Gln Ile Val Gly Gly Val Tyr Leu Leu Pro Arg Arg Gly Pro Arg
        30                  35                  40 ttg ggt gtg cgc gcg acg aga aag act tcc gag cgg tcg caa cct cga    496
Leu Gly Val Arg Ala Thr Arg Lys Thr Ser Glu Arg Ser Gln Pro Arg
    45                  50                  55 ggt aga cgt cag cct atc ccc aag gct cgt cgg ccc gag ggc agg acc    544
Gly Arg Arg Gln Pro Ile Pro Lys Ala Arg Arg Pro Glu Gly Arg Thr
60                  65                  70                  75 tgg gct cag ccc ggg tac cct tgg ccc ctc tat ggc aat gag ggc tgc    592
Trp Ala Gln Pro Gly Tyr Pro Trp Pro Leu Tyr Gly Asn Glu Gly Cys
                80                  85                  90 ggg tgg gcg gga tgg ctc ctg tct ccc cgt ggc tct cgg cct agc tgg    640
Gly Trp Ala Gly Trp Leu Leu Ser Pro Arg Gly Ser Arg Pro Ser Trp
            95                 100                 105 ggc ccc aca gac ccc cgg cgt agg tcg cgc aat ttg ggt aag gtc atc    688
Gly Pro Thr Asp Pro Arg Arg Ser Arg Asn Leu Gly Lys Val Ile
        110                 115                 120 gat acc ctt acg tgc ggc ttc gcc gac ctc atg ggg tac ata ccg ctc    736
Asp Thr Leu Thr Cys Gly Phe Ala Asp Leu Met Gly Tyr Ile Pro Leu
    125                 130                 135 gtc ggc gcc cct ctt gga ggc gct gcc agg gcc ctg gcg cat ggc gtc    784
Val Gly Ala Pro Leu Gly Gly Ala Ala Arg Ala Leu Ala His Gly Val
140                 145                 150                 155 cgg gtt ctg gaa gac ggc gtg aac tat gca aca ggg aac ctt cct ggt    832
Arg Val Leu Glu Asp Gly Val Asn Tyr Ala Thr Gly Asn Leu Pro Gly
                160                 165                 170 tgc tct ttc tct atc ttc ctt gcc ctg ctc tct tgc ttg act gtg    880
Cys Ser Phe Ser Ile Phe Leu Leu Ala Leu Leu Ser Cys Leu Thr Val
            175                 180                 185 ccc gct tcg gcc tac caa gtg cgc aac tcc acg ggg ctt tac cac gtc    928
Pro Ala Ser Ala Tyr Gln Val Arg Asn Ser Thr Gly Leu Tyr His Val
        190                 195                 200
```

```
acc aat gat tgc cct aac tcg agt att gtg tac gag gcg gcc gat gcc    976
Thr Asn Asp Cys Pro Asn Ser Ser Ile Val Tyr Glu Ala Ala Asp Ala
    205                 210                 215 atc ctg cac act ccg ggg tgc gtc cct tgc gtt cgt gag ggc aac gcc   1024
Ile Leu His Thr Pro Gly Cys Val Pro Cys Val Arg Glu Gly Asn Ala
220                 225                 230                 235 tcg agg tgt tgg gtg gcg atg acc cct acg gtg gcc acc agg gat ggc   1072
Ser Arg Cys Trp Val Ala Met Thr Pro Thr Val Ala Thr Arg Asp Gly
                240                 245                 250 aaa ctc ccc gcg acg cag ctt cga cgt cac atc gat ctg ctt gtc ggg   1120
Lys Leu Pro Ala Thr Gln Leu Arg Arg His Ile Asp Leu Leu Val Gly
            255                 260                 265 agc gcc acc ctc tgt tcg gcc ctc tac gtg ggg gac cta tgc ggg tct   1168
Ser Ala Thr Leu Cys Ser Ala Leu Tyr Val Gly Asp Leu Cys Gly Ser
        270                 275                 280 gtc ttt ctt gtc ggc caa ctg ttc acc ttc tct ccc agg cgc cac tgg   1216
Val Phe Leu Val Gly Gln Leu Phe Thr Phe Ser Pro Arg Arg His Trp
    285                 290                 295 acg acg caa ggt tgc aat tgc tct atc tat ccc ggc cat ata acg ggt   1264
Thr Thr Gln Gly Cys Asn Cys Ser Ile Tyr Pro Gly His Ile Thr Gly
300                 305                 310                 315 cac cgc atg gca tgg gat atg atg atg aac tgg tcc cct acg acg gcg   1312
His Arg Met Ala Trp Asp Met Met Met Asn Trp Ser Pro Thr Thr Ala
                320                 325                 330 ttg gta atg gct cag ctg ctc cgg atc cca caa gcc atc ttg gac atg   1360
Leu Val Met Ala Gln Leu Leu Arg Ile Pro Gln Ala Ile Leu Asp Met
            335                 340                 345 atc gct ggt gct cac tgg gga gtc ctg gcg ggc ata gcg tat ttc tcc   1408
Ile Ala Gly Ala His Trp Gly Val Leu Ala Gly Ile Ala Tyr Phe Ser
        350                 355                 360 atg gtg ggg aac tgg gcg aag gtc ctg gta gtg ctg cta ttt gcc       1456
Met Val Gly Asn Trp Ala Lys Val Leu Val Val Leu Leu Phe Ala
    365                 370                 375 ggc gtc gac gcg gaa acc cac gtc acc ggg gga agt gcc ggc cac act   1504
Gly Val Asp Ala Glu Thr His Val Thr Gly Gly Ser Ala Gly His Thr
380                 385                 390                 395 gtg tct gga ttt gtt agc ctc ctc gca cca ggc gcc aag cag aac gtc   1552
Val Ser Gly Phe Val Ser Leu Leu Ala Pro Gly Ala Lys Gln Asn Val
                400                 405                 410 cag ctg atc aac acc aac ggc agt tgg cac ctc aat agc acg gcc ctg   1600
Gln Leu Ile Asn Thr Asn Gly Ser Trp His Leu Asn Ser Thr Ala Leu
            415                 420                 425 aac tgc aat gat agc ctc aac acc ggc tgg ttg gca ggg ctt ttc tat   1648
Asn Cys Asn Asp Ser Leu Asn Thr Gly Trp Leu Ala Gly Leu Phe Tyr
        430                 435                 440 cac cac aag ttc aac tct tca ggc tgt cct gag agg cta gcc agc tgc   1696
His His Lys Phe Asn Ser Ser Gly Cys Pro Glu Arg Leu Ala Ser Cys
    445                 450                 455 cga ccc ctt acc gat ttt gac cag ggc tgg ggc cct atc agt tat gcc   1744
Arg Pro Leu Thr Asp Phe Asp Gln Gly Trp Gly Pro Ile Ser Tyr Ala
460                 465                 470                 475 aac gga agc ggc ccc gac cag cgc ccc tac tgc tgg cac tac ccc cca   1792
Asn Gly Ser Gly Pro Asp Gln Arg Pro Tyr Cys Trp His Tyr Pro Pro
                480                 485                 490 aaa cct tgc ggt att gtg ccc gcg aag agt gtg tgt ggt ccg gta tat   1840
Lys Pro Cys Gly Ile Val Pro Ala Lys Ser Val Cys Gly Pro Val Tyr
            495                 500                 505 tgc ttc act ccc agc ccc gtg gtg gtg gga acg acc gac agg tcg ggc   1888
Cys Phe Thr Pro Ser Pro Val Val Val Gly Thr Thr Asp Arg Ser Gly
        510                 515                 520
```

```
gcg ccc acc tac agc tgg ggt gaa aat gat acg gac gtc ttc gtc ctt      1936
Ala Pro Thr Tyr Ser Trp Gly Glu Asn Asp Thr Asp Val Phe Val Leu
525                 530                 535 aac aat acc agg cca ccg ctg ggc aat tgg ttc ggt tgt acc tgg atg      1984
Asn Asn Thr Arg Pro Pro Leu Gly Asn Trp Phe Gly Cys Thr Trp Met
540                 545                 550                 555 aac tca act gga ttc acc aaa gtg tgc gga gcg cct cct tgt gtc atc      2032
Asn Ser Thr Gly Phe Thr Lys Val Cys Gly Ala Pro Pro Cys Val Ile
                560                 565                 570 gga ggg gcg ggc aac aac acc ctg cac tgc ccc act gat tgc ttc cgc      2080
Gly Gly Ala Gly Asn Asn Thr Leu His Cys Pro Thr Asp Cys Phe Arg
            575                 580                 585 aag cat ccg gac gcc aca tac tct cgg tgc ggc tcc ggt ccc tgg atc      2128
Lys His Pro Asp Ala Thr Tyr Ser Arg Cys Gly Ser Gly Pro Trp Ile
        590                 595                 600 aca ccc agg tgc ctg gtc gac tac ccg tat agg ctt tgg cat tat cct      2176
Thr Pro Arg Cys Leu Val Asp Tyr Pro Tyr Arg Leu Trp His Tyr Pro
605                 610                 615 tgt acc atc aac tac acc ata ttt aaa atc agg atg tac gtg gga ggg      2224
Cys Thr Ile Asn Tyr Thr Ile Phe Lys Ile Arg Met Tyr Val Gly Gly
620                 625                 630                 635 gtc gaa cac agg ctg gaa gct gcc tgc aac tgg acg cgg ggc gaa cgt      2272
Val Glu His Arg Leu Glu Ala Ala Cys Asn Trp Thr Arg Gly Glu Arg
                640                 645                 650 tgc gat ctg gaa gac agg gac agg tcc gag ctc agc ccg tta ctg ctg      2320
Cys Asp Leu Glu Asp Arg Asp Arg Ser Glu Leu Ser Pro Leu Leu Leu
            655                 660                 665 acc act aca cag tgg cag gtc ctc ccg tgt tcc ttc aca acc cta cca      2368
Thr Thr Thr Gln Trp Gln Val Leu Pro Cys Ser Phe Thr Thr Leu Pro
        670                 675                 680 gcc ttg tcc acc ggc ctc atc cac ctc cac cag aac att gtg gac gtg      2416
Ala Leu Ser Thr Gly Leu Ile His Leu His Gln Asn Ile Val Asp Val
685                 690                 695 cag tac ttg tac ggg gtg ggg tca agc atc gcg tcc tgg gcc att aag      2464
Gln Tyr Leu Tyr Gly Val Gly Ser Ser Ile Ala Ser Trp Ala Ile Lys
700                 705                 710                 715 tgg gag tac gtc gtt ctc ctg ttc ctt ctg ctt gca gac gcg cgc gtc      2512
Trp Glu Tyr Val Val Leu Leu Phe Leu Leu Leu Ala Asp Ala Arg Val
                720                 725                 730 tgc tcc tgc ttg tgg atg atg cta ctc ata tcc caa gcg gag gcg gct      2560
Cys Ser Cys Leu Trp Met Met Leu Leu Ile Ser Gln Ala Glu Ala Ala
            735                 740                 745 ttg gag aac ctc gta ata ctt aat gca gca tcc ctg gcc ggg acg cac      2608
Leu Glu Asn Leu Val Ile Leu Asn Ala Ala Ser Leu Ala Gly Thr His
        750                 755                 760 ggt ctt gta tcc ttc ctc gtg ttc ttc tgc ttt gca tgg tat ttg aag      2656
Gly Leu Val Ser Phe Leu Val Phe Phe Cys Phe Ala Trp Tyr Leu Lys
765                 770                 775 ggt aag tgg gtg ccc gga gcg gtc tac acc ttc tac ggg atg tgg cct      2704
Gly Lys Trp Val Pro Gly Ala Val Tyr Thr Phe Tyr Gly Met Trp Pro
780                 785                 790                 795 ctc ctc ctg ctc ctg ttg gcg ttg ccc cag cgg gcg tac gcg ctg gac      2752
Leu Leu Leu Leu Leu Leu Ala Leu Pro Gln Arg Ala Tyr Ala Leu Asp
                800                 805                 810 acg gag gtg gcc gcg tcg tgt ggc ggt gtt gtt ctc gtc ggg ttg atg      2800
Thr Glu Val Ala Ala Ser Cys Gly Gly Val Val Leu Val Gly Leu Met
            815                 820                 825 gcg ctg act ctg tca cca tat tac aag cgc tat atc agc tgg tgc ttg      2848
Ala Leu Thr Leu Ser Pro Tyr Tyr Lys Arg Tyr Ile Ser Trp Cys Leu
        830                 835                 840
```

-continued

| | |
|---|---|
| tgg tgg ctt cag tat ttt ctg acc aga gtg gaa gcg caa ctg cac gtg<br>Trp Trp Leu Gln Tyr Phe Leu Thr Arg Val Glu Ala Gln Leu His Val<br>845                  850                  855 | 2896 |
| tgg att ccc ccc ctc aac gtc cga ggg ggg cgc gac gcc gtc atc tta<br>Trp Ile Pro Pro Leu Asn Val Arg Gly Gly Arg Asp Ala Val Ile Leu<br>860                  865                  870                  875 | 2944 |
| ctc atg tgt gct gta cac ccg act ctg gta ttt gac atc acc aaa ttg<br>Leu Met Cys Ala Val His Pro Thr Leu Val Phe Asp Ile Thr Lys Leu<br>                  880                  885                  890 | 2992 |
| ctg ctg gcc gtc ttc gga ccc ctt tgg att ctt caa gcc agt ttg ctt<br>Leu Leu Ala Val Phe Gly Pro Leu Trp Ile Leu Gln Ala Ser Leu Leu<br>                  895                  900                  905 | 3040 |
| aaa gta ccc tac ttt gtg cgc gtc caa ggc ctt ctc cgg ttc tgc gcg<br>Lys Val Pro Tyr Phe Val Arg Val Gln Gly Leu Leu Arg Phe Cys Ala<br>910                  915                  920 | 3088 |
| tta gcg cgg aag atg atc gga ggc cat tac gtg caa atg gtc atc att<br>Leu Ala Arg Lys Met Ile Gly Gly His Tyr Val Gln Met Val Ile Ile<br>925                  930                  935 | 3136 |
| aag tta ggg gcg ctt act ggc acc tat gtt tat aac cat ctc act cct<br>Lys Leu Gly Ala Leu Thr Gly Thr Tyr Val Tyr Asn His Leu Thr Pro<br>940                  945                  950                  955 | 3184 |
| ctt cgg gac tgg gcg cac aac ggc ttg cga gat ctg gcc gtg gct gta<br>Leu Arg Asp Trp Ala His Asn Gly Leu Arg Asp Leu Ala Val Ala Val<br>                  960                  965                  970 | 3232 |
| gag cca gtc gtc ttc tcc caa atg gag acc aag ctc atc acg tgg ggg<br>Glu Pro Val Val Phe Ser Gln Met Glu Thr Lys Leu Ile Thr Trp Gly<br>                  975                  980                  985 | 3280 |
| gca gat acc gcc gcg tgc ggt gac atc atc aac ggc ttg cct gtt tcc<br>Ala Asp Thr Ala Ala Cys Gly Asp Ile Ile Asn Gly Leu Pro Val Ser<br>                  990                  995                  1000 | 3328 |
| gcc cgc agg ggc cgg gag ata ctg ctc ggg cca gcc gat gga atg gtc<br>Ala Arg Arg Gly Arg Glu Ile Leu Leu Gly Pro Ala Asp Gly Met Val<br>1005                1010                1015 | 3376 |
| tcc aag ggg tgg agg ttg ctg gcg ccc atc acg gcg tac gcc cag cag<br>Ser Lys Gly Trp Arg Leu Leu Ala Pro Ile Thr Ala Tyr Ala Gln Gln<br>1020              1025              1030              1035 | 3424 |
| aca agg ggc ctc cta ggg tgc ata atc acc agc cta act ggc cgg gac<br>Thr Arg Gly Leu Leu Gly Cys Ile Ile Thr Ser Leu Thr Gly Arg Asp<br>                  1040              1045              1050 | 3472 |
| aaa aac caa gtg gag ggt gag gtc cag att gtg tca act gct gcc caa<br>Lys Asn Gln Val Glu Gly Glu Val Gln Ile Val Ser Thr Ala Ala Gln<br>                  1055              1060              1065 | 3520 |
| acc ttc ctg gca acg tgc atc aat ggg gtg tgc tgg act gtc tac cac<br>Thr Phe Leu Ala Thr Cys Ile Asn Gly Val Cys Trp Thr Val Tyr His<br>                  1070              1075              1080 | 3568 |
| ggg gcc gga acg agg acc atc gcg tca ccc aag ggt cct gtc atc cag<br>Gly Ala Gly Thr Arg Thr Ile Ala Ser Pro Lys Gly Pro Val Ile Gln<br>1085                1090              1095 | 3616 |
| atg tat acc aat gta gac caa gac ctt gtg ggc tgg ccc gct ccg caa<br>Met Tyr Thr Asn Val Asp Gln Asp Leu Val Gly Trp Pro Ala Pro Gln<br>1100                1105              1110              1115 | 3664 |
| ggt agc cgc tca ttg aca ccc tgc act tgc ggc tcc tcg gac ctt tac<br>Gly Ser Arg Ser Leu Thr Pro Cys Thr Cys Gly Ser Ser Asp Leu Tyr<br>                  1120              1125              1130 | 3712 |
| ctg gtc acg agg cac gcc gat gtc att ccc gtg cgc cgg cgg ggt gat<br>Leu Val Thr Arg His Ala Asp Val Ile Pro Val Arg Arg Arg Gly Asp<br>                  1135              1140              1145 | 3760 |
| agc agg ggc agc ctg ctg tcg ccc cgg ccc att tcc tac ttg aaa ggc<br>Ser Arg Gly Ser Leu Leu Ser Pro Arg Pro Ile Ser Tyr Leu Lys Gly<br>1150                1155              1160 | 3808 |

-continued

| | |
|---|---|
| tcc tcg ggg ggt ccg ctg ttg tgc ccc gcg ggg cac gcc gtg ggc ata<br>Ser Ser Gly Gly Pro Leu Leu Cys Pro Ala Gly His Ala Val Gly Ile<br>1165                     1170                      1175 | 3856 |
| ttt agg gcc gcg gtg tgc acc cgt gga gtg gct aag gcg gtg gac ttt<br>Phe Arg Ala Ala Val Cys Thr Arg Gly Val Ala Lys Ala Val Asp Phe<br>1180                     1185                     1190                     1195 | 3904 |
| atc cct gtg gag aac cta gag aca acc atg agg tcc ccg gtg ttc acg<br>Ile Pro Val Glu Asn Leu Glu Thr Thr Met Arg Ser Pro Val Phe Thr<br>                    1200                     1205                     1210 | 3952 |
| gat aac tcc tct cca cca gta gtg ccc cag agc ttc cag gtg gct cac<br>Asp Asn Ser Ser Pro Pro Val Val Pro Gln Ser Phe Gln Val Ala His<br>1215                     1220                     1225 | 4000 |
| ctc cat gct ccc aca ggc agc ggc aaa agc acc aag gtc ccg gct gca<br>Leu His Ala Pro Thr Gly Ser Gly Lys Ser Thr Lys Val Pro Ala Ala<br>             1230                     1235                     1240 | 4048 |
| tat gca gct cag ggc tat aag gtg cta gta ctc aac ccc tct gtt gct<br>Tyr Ala Ala Gln Gly Tyr Lys Val Leu Val Leu Asn Pro Ser Val Ala<br>1245                     1250                     1255 | 4096 |
| gca aca ctg ggc ttt ggt gct tac atg tcc aag gct cat ggg atc gat<br>Ala Thr Leu Gly Phe Gly Ala Tyr Met Ser Lys Ala His Gly Ile Asp<br>1260                     1265                     1270                     1275 | 4144 |
| cct aac atc agg acc ggg gtg aga aca att acc act ggc agc ccc atc<br>Pro Asn Ile Arg Thr Gly Val Arg Thr Ile Thr Thr Gly Ser Pro Ile<br>                    1280                     1285                     1290 | 4192 |
| acg tac tcc acc tac ggc aag ttc ctt gcc gac ggg ggc tgc tcg ggg<br>Thr Tyr Ser Thr Tyr Gly Lys Phe Leu Ala Asp Gly Gly Cys Ser Gly<br>1295                     1300                     1305 | 4240 |
| ggc gct tat gac ata ata att tgt gac gag tgc cac tcc acg gat gcc<br>Gly Ala Tyr Asp Ile Ile Ile Cys Asp Glu Cys His Ser Thr Asp Ala<br>             1310                     1315                     1320 | 4288 |
| aca tcc atc ttg ggc atc ggc act gtc ctt gac caa gca gag act gcg<br>Thr Ser Ile Leu Gly Ile Gly Thr Val Leu Asp Gln Ala Glu Thr Ala<br>1325                     1330                     1335 | 4336 |
| ggg gcg aga ctg gtt gtg ctc gcc acc gcc acc cct ccg ggc tcc gtc<br>Gly Ala Arg Leu Val Val Leu Ala Thr Ala Thr Pro Pro Gly Ser Val<br>1340                     1345                     1350                     1355 | 4384 |
| act gtg ccc cat ccc aac atc gag gag gtt gct ctg tcc acc acc gga<br>Thr Val Pro His Pro Asn Ile Glu Glu Val Ala Leu Ser Thr Thr Gly<br>             1360                     1365                     1370 | 4432 |
| gag atc cct ttt tac ggc aag gct atc ccc ctc gaa gta atc aag ggg<br>Glu Ile Pro Phe Tyr Gly Lys Ala Ile Pro Leu Glu Val Ile Lys Gly<br>1375                     1380                     1385 | 4480 |
| ggg aga cat ctc atc ttc tgt cat tca aag aag aag tgc gac gaa ctc<br>Gly Arg His Leu Ile Phe Cys His Ser Lys Lys Lys Cys Asp Glu Leu<br>             1390                     1395                     1400 | 4528 |
| gcc gca aag ctg gtc gca ttg ggc atc aat gcc gtg gcc tac tac cgc<br>Ala Ala Lys Leu Val Ala Leu Gly Ile Asn Ala Val Ala Tyr Tyr Arg<br>1405                     1410                     1415 | 4576 |
| ggt ctt gac gtg tcc gtc atc ccg acc agc ggc gat gtt gtc gtc gtg<br>Gly Leu Asp Val Ser Val Ile Pro Thr Ser Gly Asp Val Val Val Val<br>1420                     1425                     1430                     1435 | 4624 |
| gca acc gat gcc ctc atg acc ggc tat acc ggc gac ttc gac tcg gtg<br>Ala Thr Asp Ala Leu Met Thr Gly Tyr Thr Gly Asp Phe Asp Ser Val<br>             1440                     1445                     1450 | 4672 |
| ata gac tgc aat acg tgt gtc acc cag aca gtc gat ttc agc ctt gac<br>Ile Asp Cys Asn Thr Cys Val Thr Gln Thr Val Asp Phe Ser Leu Asp<br>1455                     1460                     1465 | 4720 |
| cct acc ttc acc att gag aca atc acg ctc ccc cag gat gct gtc tcc<br>Pro Thr Phe Thr Ile Glu Thr Ile Thr Leu Pro Gln Asp Ala Val Ser<br>             1470                     1475                     1480 | 4768 |

-continued

| | |
|---|---|
| cgc act caa cgt cgg ggc agg act ggc agg ggg aag cca ggc atc tac<br>Arg Thr Gln Arg Arg Gly Arg Thr Gly Arg Gly Lys Pro Gly Ile Tyr<br>　　　1485　　　　　　　　　1490　　　　　　　　　1495 | 4816 |
| aga ttt gtg gca ccg ggg gag cgc ccc tcc ggc atg ttc gac tcg tcc<br>Arg Phe Val Ala Pro Gly Glu Arg Pro Ser Gly Met Phe Asp Ser Ser<br>1500　　　　　　　　　1505　　　　　　　　　1510　　　　　　　　　1515 | 4864 |
| gtc ctc tgt gag tgc tat gac gca ggc tgt gct tgg tat gag ctc acg<br>Val Leu Cys Glu Cys Tyr Asp Ala Gly Cys Ala Trp Tyr Glu Leu Thr<br>　　　　　　　　　1520　　　　　　　　　1525　　　　　　　　　1530 | 4912 |
| ccc gcc gag act aca gtt agg cta cga gcg tac atg aac acc ccg ggg<br>Pro Ala Glu Thr Thr Val Arg Leu Arg Ala Tyr Met Asn Thr Pro Gly<br>　　　1535　　　　　　　　　1540　　　　　　　　　1545 | 4960 |
| ctt ccc gtg tgc cag gac cat ctt gaa ttt tgg gag ggc gtc ttt aca<br>Leu Pro Val Cys Gln Asp His Leu Glu Phe Trp Glu Gly Val Phe Thr<br>1550　　　　　　　　　1555　　　　　　　　　1560 | 5008 |
| ggc ctc act cat ata gat gcc cac ttt cta tcc cag aca aag cag agt<br>Gly Leu Thr His Ile Asp Ala His Phe Leu Ser Gln Thr Lys Gln Ser<br>　　　　　　　　　1570　　　　　　　　　1575 | 5056 |
| ggg gag aac ctt cct tac ctg gta gcg tac caa gcc acc gtg tgc gct<br>Gly Glu Asn Leu Pro Tyr Leu Val Ala Tyr Gln Ala Thr Val Cys Ala<br>1580　　　　　　　　　1585　　　　　　　　　1590　　　　　　　　　1595 | 5104 |
| agg gct caa gcc cct ccc cca tcg tgg gac cag atg tgg aag tgt ttg<br>Arg Ala Gln Ala Pro Pro Pro Ser Trp Asp Gln Met Trp Lys Cys Leu<br>　　　　　　　　　1600　　　　　　　　　1605　　　　　　　　　1610 | 5152 |
| att cgc ctc aag ccc acc ctc cat ggg cca aca ccc ctg cta tac aga<br>Ile Arg Leu Lys Pro Thr Leu His Gly Pro Thr Pro Leu Leu Tyr Arg<br>　　　1615　　　　　　　　　1620　　　　　　　　　1625 | 5200 |
| ctg ggc gct gtt cag aat gaa atc acc ctg acg cac cca gtc acc aaa<br>Leu Gly Ala Val Gln Asn Glu Ile Thr Leu Thr His Pro Val Thr Lys<br>1630　　　　　　　　　1635　　　　　　　　　1640 | 5248 |
| tac atc atg aca tgc atg tcg gcc gac ctg gag gtc gtc acg agc acc<br>Tyr Ile Met Thr Cys Met Ser Ala Asp Leu Glu Val Val Thr Ser Thr<br>　　　1645　　　　　　　　　1650　　　　　　　　　1655 | 5296 |
| tgg gtg ctc gtt ggc ggc gtc ctg gct gct ttg gcc gcg tat tgc ctg<br>Trp Val Leu Val Gly Gly Val Leu Ala Ala Leu Ala Ala Tyr Cys Leu<br>1660　　　　　　　　　1665　　　　　　　　　1670　　　　　　　　　1675 | 5344 |
| tca aca ggc tgc gtg gtc ata gtg ggc agg gtc gtc ttg tcc ggg aag<br>Ser Thr Gly Cys Val Val Ile Val Gly Arg Val Val Leu Ser Gly Lys<br>　　　　　　　　　1680　　　　　　　　　1685　　　　　　　　　1690 | 5392 |
| ccg gca atc ata cct gac agg gaa gtc ctc tac cga gag ttc gat gag<br>Pro Ala Ile Ile Pro Asp Arg Glu Val Leu Tyr Arg Glu Phe Asp Glu<br>　　　1695　　　　　　　　　1700　　　　　　　　　1705 | 5440 |
| atg gaa gag tgc tct cag cac tta ccg tac atc gag caa ggg atg atg<br>Met Glu Glu Cys Ser Gln His Leu Pro Tyr Ile Glu Gln Gly Met Met<br>1710　　　　　　　　　1715　　　　　　　　　1720 | 5488 |
| ctc gcc gag cag ttc aag cag aag gcc ctc ggc ctc ctg cag acc gcg<br>Leu Ala Glu Gln Phe Lys Gln Lys Ala Leu Gly Leu Leu Gln Thr Ala<br>　　　1725　　　　　　　　　1730　　　　　　　　　1735 | 5536 |
| tcc cgt cag gca gag gtt atc gcc cct gct gtc cag acc aac tgg caa<br>Ser Arg Gln Ala Glu Val Ile Ala Pro Ala Val Gln Thr Asn Trp Gln<br>1740　　　　　　　　　1745　　　　　　　　　1750　　　　　　　　　1755 | 5584 |
| aaa ctc gag acc ttc tgg gcg aag cat atg tgg aac ttc atc agt ggg<br>Lys Leu Glu Thr Phe Trp Ala Lys His Met Trp Asn Phe Ile Ser Gly<br>　　　　　　　　　1760　　　　　　　　　1765　　　　　　　　　1770 | 5632 |
| ata caa tac ttg gcg ggc ttg tca acg ctg cct ggt aac ccc gcc att<br>Ile Gln Tyr Leu Ala Gly Leu Ser Thr Leu Pro Gly Asn Pro Ala Ile<br>　　　1775　　　　　　　　　1780　　　　　　　　　1785 | 5680 |
| gct tca ttg atg gct ttt aca gct gct gtc acc agc cca cta acc act<br>Ala Ser Leu Met Ala Phe Thr Ala Ala Val Thr Ser Pro Leu Thr Thr<br>1790　　　　　　　　　1795　　　　　　　　　1800 | 5728 |

```
agc caa acc ctc ctc ttc aac ata ttg ggg ggg tgg gtg gct gcc cag      5776
Ser Gln Thr Leu Leu Phe Asn Ile Leu Gly Gly Trp Val Ala Ala Gln
    1805                1810                1815 ctc gcc gcc ccc ggt gcc gct act gcc ttt gtg ggc gct ggc tta gct      5824
Leu Ala Ala Pro Gly Ala Ala Thr Ala Phe Val Gly Ala Gly Leu Ala
1820                1825                1830                1835 ggc gcc gcc atc ggc agt gtt gga ctg ggg aag gtc ctc ata gac atc      5872
Gly Ala Ala Ile Gly Ser Val Gly Leu Gly Lys Val Leu Ile Asp Ile
                1840                1845                1850 ctt gca ggg tat ggc gcg ggc gtg gcg gga gct ctt gtg gca ttc aag      5920
Leu Ala Gly Tyr Gly Ala Gly Val Ala Gly Ala Leu Val Ala Phe Lys
            1855                1860                1865 atc atg agc ggt gag gtc ccc tcc acg gag gac ctg gtc aat cta ctg      5968
Ile Met Ser Gly Glu Val Pro Ser Thr Glu Asp Leu Val Asn Leu Leu
        1870                1875                1880 ccc gcc atc ctc tcg ccc gga gcc ctc gta gtc ggc gtg gtc tgt gca      6016
Pro Ala Ile Leu Ser Pro Gly Ala Leu Val Val Gly Val Val Cys Ala
    1885                1890                1895 gca ata ctg cgc cgg cac gtt ggc ccg ggc gag ggg gca gtg cag tgg      6064
Ala Ile Leu Arg Arg His Val Gly Pro Gly Glu Gly Ala Val Gln Trp
1900                1905                1910                1915 atg aac cgg ctg ata gcc ttc gcc tcc cgg ggg aac cat gtt tcc ccc      6112
Met Asn Arg Leu Ile Ala Phe Ala Ser Arg Gly Asn His Val Ser Pro
                1920                1925                1930 acg cac tac gtg ccg gag agc gat gca gct gcc cgc gtc act gcc ata      6160
Thr His Tyr Val Pro Glu Ser Asp Ala Ala Ala Arg Val Thr Ala Ile
            1935                1940                1945 ctc agc agc ctc act gta acc cag ctc ctg agg cga ctg cac cag tgg      6208
Leu Ser Ser Leu Thr Val Thr Gln Leu Leu Arg Arg Leu His Gln Trp
        1950                1955                1960 ata agc tcg gag tgt acc act cca tgc tcc ggt tcc tgg cta agg gac      6256
Ile Ser Ser Glu Cys Thr Thr Pro Cys Ser Gly Ser Trp Leu Arg Asp
    1965                1970                1975 atc tgg gac tgg ata tgc gag gtg ttg agc gac ttt aag acc tgg cta      6304
Ile Trp Asp Trp Ile Cys Glu Val Leu Ser Asp Phe Lys Thr Trp Leu
1980                1985                1990                1995 aaa gct aag ctc atg cca cag ctg cct ggg atc ccc ttt gtg tcc tgc      6352
Lys Ala Lys Leu Met Pro Gln Leu Pro Gly Ile Pro Phe Val Ser Cys
                2000                2005                2010 cag cgc ggg tat aag ggg gtc tgg cga gtg gac ggc atc atg cac act      6400
Gln Arg Gly Tyr Lys Gly Val Trp Arg Val Asp Gly Ile Met His Thr
            2015                2020                2025 cgc tgc cac tgt gga gct gag atc act gga cat gtc aaa aac ggg acg      6448
Arg Cys His Cys Gly Ala Glu Ile Thr Gly His Val Lys Asn Gly Thr
        2030                2035                2040 atg agg atc gtc ggt cct agg acc tgc agg aac atg tgg agt ggg acc      6496
Met Arg Ile Val Gly Pro Arg Thr Cys Arg Asn Met Trp Ser Gly Thr
    2045                2050                2055 ttc ccc att aat gcc tac acc acg ggc ccc tgt acc ccc ctt cct gcg      6544
Phe Pro Ile Asn Ala Tyr Thr Thr Gly Pro Cys Thr Pro Leu Pro Ala
2060                2065                2070                2075 ccg aac tac acg ttc gcg cta tgg agg gtg tct gca gag gaa tat gtg      6592
Pro Asn Tyr Thr Phe Ala Leu Trp Arg Val Ser Ala Glu Glu Tyr Val
                2080                2085                2090 gag ata agg cag gtg ggg gac ttc cac tac gtg acg ggt atg act act      6640
Glu Ile Arg Gln Val Gly Asp Phe His Tyr Val Thr Gly Met Thr Thr
            2095                2100                2105 gac aat ctc aaa tgc ccg tgc cag gtc cca tcg ccc gaa ttt ttc aca      6688
Asp Asn Leu Lys Cys Pro Cys Gln Val Pro Ser Pro Glu Phe Phe Thr
        2110                2115                2120
```

```
-continued gaa ttg gac ggg gtg cgc cta cat agg ttt gcg ccc ccc tgc aag ccc      6736
Glu Leu Asp Gly Val Arg Leu His Arg Phe Ala Pro Pro Cys Lys Pro
    2125                2130                2135 ttg ctg cgg gag gag gta tca ttc aga gta gga ctc cac gaa tac ccg      6784
Leu Leu Arg Glu Glu Val Ser Phe Arg Val Gly Leu His Glu Tyr Pro
2140                2145                2150                2155 gta ggg tcg caa tta cct tgc gag ccc gaa ccg gac gtg gcc gtg ttg      6832
Val Gly Ser Gln Leu Pro Cys Glu Pro Glu Pro Asp Val Ala Val Leu
                2160                2165                2170 acg tcc atg ctc act gat ccc tcc cat ata aca gca gag gcg gcc ggg      6880
Thr Ser Met Leu Thr Asp Pro Ser His Ile Thr Ala Glu Ala Ala Gly
            2175                2180                2185 cga agg ttg gcg agg gga tca ccc ccc tct gtg gcc agc tcc tcg gct      6928
Arg Arg Leu Ala Arg Gly Ser Pro Pro Ser Val Ala Ser Ser Ser Ala
        2190                2195                2200 agc cag cta tcc gct cca tct ctc aag gca act tgc acc gct aac cat      6976
Ser Gln Leu Ser Ala Pro Ser Leu Lys Ala Thr Cys Thr Ala Asn His
    2205                2210                2215 gac tcc cct gat gct gag ctc ata gag gcc aac ctc cta tgg agg cag      7024
Asp Ser Pro Asp Ala Glu Leu Ile Glu Ala Asn Leu Leu Trp Arg Gln
2220                2225                2230                2235 gag atg ggc ggc aac atc acc agg gtt gag tca gaa aac aaa gtg gtg      7072
Glu Met Gly Gly Asn Ile Thr Arg Val Glu Ser Glu Asn Lys Val Val
                2240                2245                2250 att ctg gac tcc ttc gat ccg ctt gtg gcg gag gag gac gag cgg gag      7120
Ile Leu Asp Ser Phe Asp Pro Leu Val Ala Glu Glu Asp Glu Arg Glu
            2255                2260                2265 atc tcc gta ccc gca gaa atc ctg cgg aag tct cgg aga ttc gcc cag      7168
Ile Ser Val Pro Ala Glu Ile Leu Arg Lys Ser Arg Arg Phe Ala Gln
        2270                2275                2280 gcc ctg ccc gtt tgg gcg cgg ccg gac tat aac ccc ccg cta gtg gag      7216
Ala Leu Pro Val Trp Ala Arg Pro Asp Tyr Asn Pro Pro Leu Val Glu
    2285                2290                2295 acg tgg aaa aag ccc gac tac gaa cca cct gtg gtc cat ggc tgt ccg      7264
Thr Trp Lys Lys Pro Asp Tyr Glu Pro Pro Val Val His Gly Cys Pro
2300                2305                2310                2315 ctt cca cct cca aag tcc cct cct gtg cct ccg cct cgg aag aag cgg      7312
Leu Pro Pro Pro Lys Ser Pro Pro Val Pro Pro Pro Arg Lys Lys Arg
                2320                2325                2330 acg gtg gtc ctc act gaa tca acc cta tct act gcc ttg gcc gag ctc      7360
Thr Val Val Leu Thr Glu Ser Thr Leu Ser Thr Ala Leu Ala Glu Leu
            2335                2340                2345 gcc acc aga agc ttt ggc agc tcc tca act tcc ggc att acg ggc gac      7408
Ala Thr Arg Ser Phe Gly Ser Ser Ser Thr Ser Gly Ile Thr Gly Asp
        2350                2355                2360 aat acg aca aca tcc tct gag ccc gcc cct tct ggc tgc ccc ccc gac      7456
Asn Thr Thr Thr Ser Ser Glu Pro Ala Pro Ser Gly Cys Pro Pro Asp
    2365                2370                2375 tcc gac gct gag tcc tat tcc tcc atg ccc ccc ctg gag ggg gag cct      7504
Ser Asp Ala Glu Ser Tyr Ser Ser Met Pro Pro Leu Glu Gly Glu Pro
2380                2385                2390                2395 ggg gat ccg gat ctt agc gac ggg tca tgg tca acg gtc agt agt gag      7552
Gly Asp Pro Asp Leu Ser Asp Gly Ser Trp Ser Thr Val Ser Ser Glu
                2400                2405                2410 gcc aac gcg gag gat gtc gtg tgc tgc tca atg tct tac tct tgg aca      7600
Ala Asn Ala Glu Asp Val Val Cys Cys Ser Met Ser Tyr Ser Trp Thr
            2415                2420                2425 ggc gca ctc gtc acc ccg tgc gcc gcg gaa gaa cag aaa ctg ccc atc      7648
Gly Ala Leu Val Thr Pro Cys Ala Ala Glu Glu Gln Lys Leu Pro Ile
        2430                2435                2440
```

-continued

| | | |
|---|---|---|
| aat gca cta agc aac tcg ttg cta cgt cac cac aat ttg gtg tat tcc<br>Asn Ala Leu Ser Asn Ser Leu Leu Arg His His Asn Leu Val Tyr Ser<br>              2445                        2450                        2455 | 7696 |
| acc acc tca cgc agt gct tgc caa agg cag aag aaa gtc aca ttt gac<br>Thr Thr Ser Arg Ser Ala Cys Gln Arg Gln Lys Lys Val Thr Phe Asp<br>2460                        2465                        2470                        2475 | 7744 |
| aga ctg caa gtt ctg gac agc cat tac cag gac gta ctc aag gag gtt<br>Arg Leu Gln Val Leu Asp Ser His Tyr Gln Asp Val Leu Lys Glu Val<br>                      2480                        2485                        2490 | 7792 |
| aaa gca gcg gcg tca aaa gtg aag gct aac ttg cta tcc gta gag gaa<br>Lys Ala Ala Ala Ser Lys Val Lys Ala Asn Leu Leu Ser Val Glu Glu<br>              2495                        2500                        2505 | 7840 |
| gct tgc agc ctg acg ccc cca cac tca gcc aaa tcc aag ttt ggt tat<br>Ala Cys Ser Leu Thr Pro Pro His Ser Ala Lys Ser Lys Phe Gly Tyr<br>                      2510                        2515                        2520 | 7888 |
| ggg gca aaa gac gtc cgt tgc cat gcc aga aag gcc gta acc cac atc<br>Gly Ala Lys Asp Val Arg Cys His Ala Arg Lys Ala Val Thr His Ile<br>            2525                        2530                        2535 | 7936 |
| aac tcc gtg tgg aaa gac ctt ctg gaa gac aat gta aca cca ata gac<br>Asn Ser Val Trp Lys Asp Leu Leu Glu Asp Asn Val Thr Pro Ile Asp<br>2540                        2545                        2550                        2555 | 7984 |
| act acc atc atg gct aag aac gag gtt ttc tgc gtt cag cct gag aag<br>Thr Thr Ile Met Ala Lys Asn Glu Val Phe Cys Val Gln Pro Glu Lys<br>                      2560                        2565                        2570 | 8032 |
| ggg ggt cgt aag cca gct cgt ctc atc gtg ttc ccc gat ctg ggc gtg<br>Gly Gly Arg Lys Pro Ala Arg Leu Ile Val Phe Pro Asp Leu Gly Val<br>            2575                        2580                        2585 | 8080 |
| cgc gtg tgc gaa aag atg gct ttg tac gac gtg gtt aca aag ctc ccc<br>Arg Val Cys Glu Lys Met Ala Leu Tyr Asp Val Val Thr Lys Leu Pro<br>                      2590                        2595                        2600 | 8128 |
| ttg gcc gtg atg gga agc tcc tac gga ttc caa tac tca cca gga cag<br>Leu Ala Val Met Gly Ser Ser Tyr Gly Phe Gln Tyr Ser Pro Gly Gln<br>2605                        2610                        2615 | 8176 |
| cgg gtt gaa ttc ctc gtg caa gcg tgg aag tcc aag aaa acc cca atg<br>Arg Val Glu Phe Leu Val Gln Ala Trp Lys Ser Lys Lys Thr Pro Met<br>2620                        2625                        2630                        2635 | 8224 |
| ggg ttc tcg tat gat acc cgc tgc ttt gac tcc aca gtc act gag agc<br>Gly Phe Ser Tyr Asp Thr Arg Cys Phe Asp Ser Thr Val Thr Glu Ser<br>                      2640                        2645                        2650 | 8272 |
| gac atc cgt acg gag gag gca atc tac caa tgt tgt gac ctc gac ccc<br>Asp Ile Arg Thr Glu Glu Ala Ile Tyr Gln Cys Cys Asp Leu Asp Pro<br>            2655                        2660                        2665 | 8320 |
| caa gcc cgc gtg gcc atc aag tcc ctc acc gag agg ctt tat gtt ggg<br>Gln Ala Arg Val Ala Ile Lys Ser Leu Thr Glu Arg Leu Tyr Val Gly<br>                      2670                        2675                        2680 | 8368 |
| ggc cct ctt acc aat tca agg ggg gag aac tgc ggc tat cgc agg tgc<br>Gly Pro Leu Thr Asn Ser Arg Gly Glu Asn Cys Gly Tyr Arg Arg Cys<br>2685                        2690                        2695 | 8416 |
| cgc gcg agc ggc gta ctg aca act agc tgt ggt aac acc ctc act tgc<br>Arg Ala Ser Gly Val Leu Thr Thr Ser Cys Gly Asn Thr Leu Thr Cys<br>2700                        2705                        2710                        2715 | 8464 |
| tac atc aag gcc cgg gca gcc tgt cga gcc gca ggg ctc cag gac tgc<br>Tyr Ile Lys Ala Arg Ala Ala Cys Arg Ala Ala Gly Leu Gln Asp Cys<br>                      2720                        2725                        2730 | 8512 |

```
acc atg ctc gtg tgt ggc gac gac tta gtc gtt atc tgt gaa agc gcg      8560
Thr Met Leu Val Cys Gly Asp Asp Leu Val Val Ile Cys Glu Ser Ala
        2735                2740                2745 ggg gtc cag gag gac gcg gcg agc ctg aga gcc ttc acg gag gct atg      8608
Gly Val Gln Glu Asp Ala Ala Ser Leu Arg Ala Phe Thr Glu Ala Met
    2750                2755                2760 acc agg tac tcc gcc ccc cct ggg gac ccc cca caa cca gaa tac gac      8656
Thr Arg Tyr Ser Ala Pro Pro Gly Asp Pro Pro Gln Pro Glu Tyr Asp
    2765                2770                2775 ttg gag ctc ata aca tca tgc tcc tcc aac gtg tca gtc gcc cac gac      8704
Leu Glu Leu Ile Thr Ser Cys Ser Ser Asn Val Ser Val Ala His Asp
2780                2785                2790                2795 ggc gct gga aag agg gtc tac tac ctc acc cgt gac cct aca acc ccc      8752
Gly Ala Gly Lys Arg Val Tyr Tyr Leu Thr Arg Asp Pro Thr Thr Pro
            2800                2805                2810 ctc gcg aga gct gcg tgg gag aca gca aga cac act cca gtc aat tcc      8800
Leu Ala Arg Ala Ala Trp Glu Thr Ala Arg His Thr Pro Val Asn Ser
        2815                2820                2825 tgg cta ggc aac ata atc atg ttt gcc ccc aca ctg tgg gcg agg atg      8848
Trp Leu Gly Asn Ile Ile Met Phe Ala Pro Thr Leu Trp Ala Arg Met
    2830                2835                2840 ata ctg atg acc cat ttc ttt agc gtc ctt ata gcc agg gac cag ctt      8896
Ile Leu Met Thr His Phe Phe Ser Val Leu Ile Ala Arg Asp Gln Leu
    2845                2850                2855 gaa cag gcc ctc gat tgc gag atc tac ggg gcc tgc tac tcc ata gaa      8944
Glu Gln Ala Leu Asp Cys Glu Ile Tyr Gly Ala Cys Tyr Ser Ile Glu
2860                2865                2870                2875 cca ctt gat cta cct cca atc att caa aga ctc cat ggc ctc agc gca      8992
Pro Leu Asp Leu Pro Pro Ile Ile Gln Arg Leu His Gly Leu Ser Ala
            2880                2885                2890 ttt tca ctc cac agt tac tct cca ggt gaa att aat agg gtg gcc gca      9040
Phe Ser Leu His Ser Tyr Ser Pro Gly Glu Ile Asn Arg Val Ala Ala
        2895                2900                2905 tgc ctc aga aaa ctt ggg gta ccg ccc ttg cga gct tgg aga cac cgg      9088
Cys Leu Arg Lys Leu Gly Val Pro Pro Leu Arg Ala Trp Arg His Arg
    2910                2915                2920 gcc cgg agc gtc cgc gct agg ctt ctg gcc aga gga ggc agg gct gcc      9136
Ala Arg Ser Val Arg Ala Arg Leu Leu Ala Arg Gly Gly Arg Ala Ala
    2925                2930                2935 ata tgt ggc aag tac ctc ttc aac tgg gca gta aga aca aag ctc aaa      9184
Ile Cys Gly Lys Tyr Leu Phe Asn Trp Ala Val Arg Thr Lys Leu Lys
2940                2945                2950                2955 ctc act cca ata gcg gcc gct ggc cag ctg gac ttg tcc ggc tgg ttc      9232
Leu Thr Pro Ile Ala Ala Ala Gly Gln Leu Asp Leu Ser Gly Trp Phe
            2960                2965                2970 acg gct ggc tac agc ggg gga gac att tat cac agc gtg tct cat gcc      9280
Thr Ala Gly Tyr Ser Gly Gly Asp Ile Tyr His Ser Val Ser His Ala
        2975                2980                2985 cgg ccc cgc tgg atc tgg ttt tgc cta ctc ctg ctt gct gca ggg gta      9328
Arg Pro Arg Trp Ile Trp Phe Cys Leu Leu Leu Ala Ala Gly Val
    2990                2995                3000 ggc atc tac ctc ctc ccc aac cga tgaaggttgg ggtaaacact ccggcct        9379
Gly Ile Tyr Leu Leu Pro Asn Arg
        3005                3010

<210> SEQ ID NO 2
<211> LENGTH: 3011
<212> TYPE: PRT
<213> ORGANISM: Virus
```

-continued

<400> SEQUENCE: 2

```
Met Ser Thr Asn Pro Lys Pro Gln Lys Lys Asn Lys Arg Asn Thr Asn
 1               5                  10                  15
Arg Arg Pro Gln Asp Val Lys Phe Pro Gly Gly Gln Ile Val Gly
             20                  25                  30
Gly Val Tyr Leu Leu Pro Arg Arg Gly Pro Arg Leu Gly Val Arg Ala
             35                  40                  45
Thr Arg Lys Thr Ser Glu Arg Ser Gln Pro Arg Gly Arg Arg Gln Pro
 50                  55                  60
Ile Pro Lys Ala Arg Arg Pro Glu Gly Arg Thr Trp Ala Gln Pro Gly
 65                  70                  75                  80
Tyr Pro Trp Pro Leu Tyr Gly Asn Glu Gly Cys Gly Trp Ala Gly Trp
                 85                  90                  95
Leu Leu Ser Pro Arg Gly Ser Arg Pro Ser Trp Gly Pro Thr Asp Pro
                100                 105                 110
Arg Arg Arg Ser Arg Asn Leu Gly Lys Val Ile Asp Thr Leu Thr Cys
                115                 120                 125
Gly Phe Ala Asp Leu Met Gly Tyr Ile Pro Leu Val Gly Ala Pro Leu
                130                 135                 140
Gly Gly Ala Ala Arg Ala Leu Ala His Gly Val Arg Val Leu Glu Asp
145                 150                 155                 160
Gly Val Asn Tyr Ala Thr Gly Asn Leu Pro Gly Cys Ser Phe Ser Ile
                165                 170                 175
Phe Leu Leu Ala Leu Leu Ser Cys Leu Thr Val Pro Ala Ser Ala Tyr
                180                 185                 190
Gln Val Arg Asn Ser Thr Gly Leu Tyr His Val Thr Asn Asp Cys Pro
                195                 200                 205
Asn Ser Ser Ile Val Tyr Glu Ala Ala Asp Ala Ile Leu His Thr Pro
                210                 215                 220
Gly Cys Val Pro Cys Val Arg Glu Gly Asn Ala Ser Arg Cys Trp Val
225                 230                 235                 240
Ala Met Thr Pro Thr Val Ala Thr Arg Asp Gly Lys Leu Pro Ala Thr
                245                 250                 255
Gln Leu Arg Arg His Ile Asp Leu Leu Val Gly Ser Ala Thr Leu Cys
                260                 265                 270
Ser Ala Leu Tyr Val Gly Asp Leu Cys Gly Ser Val Phe Leu Val Gly
                275                 280                 285
Gln Leu Phe Thr Phe Ser Pro Arg Arg His Trp Thr Thr Gln Gly Cys
                290                 295                 300
Asn Cys Ser Ile Tyr Pro Gly His Ile Thr Gly His Arg Met Ala Trp
305                 310                 315                 320
```

-continued

```
Asp Met Met Met Asn Trp Ser Pro Thr Thr Ala Leu Val Met Ala Gln
            325                 330                 335

Leu Leu Arg Ile Pro Gln Ala Ile Leu Asp Met Ile Ala Gly Ala His
        340                 345                 350

Trp Gly Val Leu Ala Gly Ile Ala Tyr Phe Ser Met Val Gly Asn Trp
    355                 360                 365

Ala Lys Val Leu Val Leu Leu Phe Ala Gly Val Asp Ala Glu
370                 375                 380

Thr His Val Thr Gly Gly Ser Ala Gly His Thr Val Ser Gly Phe Val
385                 390                 395                 400

Ser Leu Leu Ala Pro Gly Ala Lys Gln Asn Val Gln Leu Ile Asn Thr
                405                 410                 415

Asn Gly Ser Trp His Leu Asn Ser Thr Ala Leu Asn Cys Asn Asp Ser
            420                 425                 430

Leu Asn Thr Gly Trp Leu Ala Gly Leu Phe Tyr His His Lys Phe Asn
        435                 440                 445

Ser Ser Gly Cys Pro Glu Arg Leu Ala Ser Cys Arg Pro Leu Thr Asp
    450                 455                 460

Phe Asp Gln Gly Trp Gly Pro Ile Ser Tyr Ala Asn Gly Ser Gly Pro
465                 470                 475                 480

Asp Gln Arg Pro Tyr Cys Trp His Tyr Pro Lys Pro Cys Gly Ile
                485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
        515                 520                 525

Trp Gly Glu Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Ala Gly Asn
                565                 570                 575

Asn Thr Leu His Cys Pro Thr Asp Cys Phe Arg Lys His Pro Asp Ala
            580                 585                 590

Thr Tyr Ser Arg Cys Gly Ser Gly Pro Trp Ile Thr Pro Arg Cys Leu
        595                 600                 605

Val Asp Tyr Pro Tyr Arg Leu Trp His Tyr Pro Cys Thr Ile Asn Tyr
    610                 615                 620

Thr Ile Phe Lys Ile Arg Met Tyr Val Gly Gly Val Glu His Arg Leu
625                 630                 635                 640
```

```
Glu Ala Ala Cys Asn Trp Thr Arg Gly Glu Arg Cys Asp Leu Glu Asp
                645                 650                 655

Arg Asp Arg Ser Glu Leu Ser Pro Leu Leu Thr Thr Thr Gln Trp
        660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
        690                 695                 700

Val Gly Ser Ser Ile Ala Ser Trp Ala Ile Lys Trp Glu Tyr Val Val
705                 710                 715                 720

Leu Leu Phe Leu Leu Ala Asp Ala Arg Val Cys Ser Cys Leu Trp
            725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
            755                 760                 765

Leu Val Phe Phe Cys Phe Ala Trp Tyr Leu Lys Gly Lys Trp Val Pro
    770                 775                 780

Gly Ala Val Tyr Thr Phe Tyr Gly Met Trp Pro Leu Leu Leu Leu
785                 790                 795                 800

Leu Ala Leu Pro Gln Arg Ala Tyr Ala Leu Asp Thr Glu Val Ala Ala
            805                 810                 815

Ser Cys Gly Gly Val Val Leu Val Gly Leu Met Ala Leu Thr Leu Ser
        820                 825                 830

Pro Tyr Tyr Lys Arg Tyr Ile Ser Trp Cys Leu Trp Trp Leu Gln Tyr
        835                 840                 845

Phe Leu Thr Arg Val Glu Ala Gln Leu His Val Trp Ile Pro Pro Leu
    850                 855                 860

Asn Val Arg Gly Gly Arg Asp Ala Val Ile Leu Met Cys Ala Val
865                 870                 875                 880

His Pro Thr Leu Val Phe Asp Ile Thr Lys Leu Leu Leu Ala Val Phe
            885                 890                 895

Gly Pro Leu Trp Ile Leu Gln Ala Ser Leu Leu Lys Val Pro Tyr Phe
            900                 905                 910

Val Arg Val Gln Gly Leu Leu Arg Phe Cys Ala Leu Ala Arg Lys Met
        915                 920                 925

Ile Gly Gly His Tyr Val Gln Met Val Ile Lys Leu Gly Ala Leu
        930                 935                 940

Thr Gly Thr Tyr Val Tyr Asn His Leu Thr Pro Leu Arg Asp Trp Ala
945                 950                 955                 960
```

-continued

His Asn Gly Leu Arg Asp Leu Ala Val Ala Val Glu Pro Val Val Phe
            965                 970                 975

Ser Gln Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Arg
            995                 1000                1005

Glu Ile Leu Leu Gly Pro Ala Asp Gly Met Val Ser Lys Gly Trp Arg
            1010                1015                1020

Leu Leu Ala Pro Ile Thr Ala Tyr Ala Gln Gln Thr Arg Gly Leu Leu
1025                1030                1035                1040

Gly Cys Ile Ile Thr Ser Leu Thr Gly Arg Asp Lys Asn Gln Val Glu
            1045                1050                1055

Gly Glu Val Gln Ile Val Ser Thr Ala Ala Gln Thr Phe Leu Ala Thr
            1060                1065                1070

Cys Ile Asn Gly Val Cys Trp Thr Val Tyr His Gly Ala Gly Thr Arg
            1075                1080                1085

Thr Ile Ala Ser Pro Lys Gly Pro Val Ile Gln Met Tyr Thr Asn Val
            1090                1095                1100

Asp Gln Asp Leu Val Gly Trp Pro Ala Pro Gln Gly Ser Arg Ser Leu
1105                1110                1115                1120

Thr Pro Cys Thr Cys Gly Ser Ser Asp Leu Tyr Leu Val Thr Arg His
            1125                1130                1135

Ala Asp Val Ile Pro Val Arg Arg Arg Gly Asp Ser Arg Gly Ser Leu
            1140                1145                1150

Leu Ser Pro Arg Pro Ile Ser Tyr Leu Lys Gly Ser Ser Gly Gly Pro
            1155                1160                1165

Leu Leu Cys Pro Ala Gly His Ala Val Gly Ile Phe Arg Ala Ala Val
            1170                1175                1180

Cys Thr Arg Gly Val Ala Lys Ala Val Asp Phe Ile Pro Val Glu Asn
1185                1190                1195                1200

Leu Glu Thr Thr Met Arg Ser Pro Val Phe Thr Asp Asn Ser Ser Pro
            1205                1210                1215

Pro Val Val Pro Gln Ser Phe Gln Val Ala His Leu His Ala Pro Thr
            1220                1225                1230

Gly Ser Gly Lys Ser Thr Lys Val Pro Ala Ala Tyr Ala Ala Gln Gly
            1235                1240                1245

Tyr Lys Val Leu Val Leu Asn Pro Ser Val Ala Ala Thr Leu Gly Phe
            1250                1255                1260

Gly Ala Tyr Met Ser Lys Ala His Gly Ile Asp Pro Asn Ile Arg Thr
1265                1270                1275                1280

-continued

```
Gly Val Arg Thr Ile Thr Thr Gly Ser Pro Ile Thr Tyr Ser Thr Tyr
            1285                1290                1295

Gly Lys Phe Leu Ala Asp Gly Gly Cys Ser Gly Gly Ala Tyr Asp Ile
            1300                1305                1310

Ile Ile Cys Asp Glu Cys His Ser Thr Asp Ala Thr Ser Ile Leu Gly
            1315                1320                1325

Ile Gly Thr Val Leu Asp Gln Ala Glu Thr Ala Gly Ala Arg Leu Val
            1330                1335                1340

Val Leu Ala Thr Ala Thr Pro Pro Gly Ser Val Thr Val Pro His Pro
1345                1350                1355                1360

Asn Ile Glu Glu Val Ala Leu Ser Thr Thr Gly Glu Ile Pro Phe Tyr
            1365                1370                1375

Gly Lys Ala Ile Pro Leu Glu Val Ile Lys Gly Gly Arg His Leu Ile
            1380                1385                1390

Phe Cys His Ser Lys Lys Cys Asp Glu Leu Ala Ala Lys Leu Val
            1395                1400                1405

Ala Leu Gly Ile Asn Ala Val Ala Tyr Tyr Arg Gly Leu Asp Val Ser
            1410                1415                1420

Val Ile Pro Thr Ser Gly Asp Val Val Val Ala Thr Asp Ala Leu
1425                1430                1435                1440

Met Thr Gly Tyr Thr Gly Asp Phe Asp Ser Val Ile Asp Cys Asn Thr
            1445                1450                1455

Cys Val Thr Gln Thr Val Asp Phe Ser Leu Asp Pro Thr Phe Thr Ile
            1460                1465                1470

Glu Thr Ile Thr Leu Pro Gln Asp Ala Val Ser Arg Thr Gln Arg Arg
            1475                1480                1485

Gly Arg Thr Gly Arg Gly Lys Pro Gly Ile Tyr Arg Phe Val Ala Pro
            1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Thr
            1525                1530                1535

Val Arg Leu Arg Ala Tyr Met Asn Thr Pro Gly Leu Pro Val Cys Gln
            1540                1545                1550

Asp His Leu Glu Phe Trp Glu Gly Val Phe Thr Gly Leu Thr His Ile
            1555                1560                1565

Asp Ala His Phe Leu Ser Gln Thr Lys Gln Ser Gly Glu Asn Leu Pro
            1570                1575                1580

Tyr Leu Val Ala Tyr Gln Ala Thr Val Cys Ala Arg Ala Gln Ala Pro
1585                1590                1595                1600
```

-continued

Pro Pro Ser Trp Asp Gln Met Trp Lys Cys Leu Ile Arg Leu Lys Pro
            1605                1610                1615

Thr Leu His Gly Pro Thr Pro Leu Leu Tyr Arg Leu Gly Ala Val Gln
        1620                1625                1630

Asn Glu Ile Thr Leu Thr His Pro Val Thr Lys Tyr Ile Met Thr Cys
        1635                1640                1645

Met Ser Ala Asp Leu Glu Val Val Thr Ser Thr Trp Val Leu Val Gly
        1650                1655                1660

Gly Val Leu Ala Ala Leu Ala Ala Tyr Cys Leu Ser Thr Gly Cys Val
1665                1670                1675                1680

Val Ile Val Gly Arg Val Val Leu Ser Gly Lys Pro Ala Ile Ile Pro
            1685                1690                1695

Asp Arg Glu Val Leu Tyr Arg Glu Phe Asp Glu Met Glu Glu Cys Ser
            1700                1705                1710

Gln His Leu Pro Tyr Ile Glu Gln Gly Met Met Leu Ala Glu Gln Phe
            1715                1720                1725

Lys Gln Lys Ala Leu Gly Leu Leu Gln Thr Ala Ser Arg Gln Ala Glu
            1730                1735                1740

Val Ile Ala Pro Ala Val Gln Thr Asn Trp Gln Lys Leu Glu Thr Phe
1745                1750                1755                1760

Trp Ala Lys His Met Trp Asn Phe Ile Ser Gly Ile Gln Tyr Leu Ala
            1765                1770                1775

Gly Leu Ser Thr Leu Pro Gly Asn Pro Ala Ile Ala Ser Leu Met Ala
            1780                1785                1790

Phe Thr Ala Ala Val Thr Ser Pro Leu Thr Thr Ser Gln Thr Leu Leu
            1795                1800                1805

Phe Asn Ile Leu Gly Gly Trp Val Ala Ala Gln Leu Ala Ala Pro Gly
            1810                1815                1820

Ala Ala Thr Ala Phe Val Gly Ala Gly Leu Ala Gly Ala Ala Ile Gly
1825                1830                1835                1840

Ser Val Gly Leu Gly Lys Val Leu Ile Asp Ile Leu Ala Gly Tyr Gly
            1845                1850                1855

Ala Gly Val Ala Gly Ala Leu Val Ala Phe Lys Ile Met Ser Gly Glu
            1860                1865                1870

Val Pro Ser Thr Glu Asp Leu Val Asn Leu Leu Pro Ala Ile Leu Ser
            1875                1880                1885

Pro Gly Ala Leu Val Val Gly Val Val Cys Ala Ala Ile Leu Arg Arg
            1890                1895                1900

His Val Gly Pro Gly Glu Gly Ala Val Gln Trp Met Asn Arg Leu Ile
1905                1910                1915                1920

-continued

Ala Phe Ala Ser Arg Gly Asn His Val Ser Pro Thr His Tyr Val Pro
              1925                1930                1935

Glu Ser Asp Ala Ala Arg Val Thr Ala Ile Leu Ser Ser Leu Thr
        1940                1945                1950

Val Thr Gln Leu Leu Arg Arg Leu His Gln Trp Ile Ser Ser Glu Cys
        1955                1960                1965

Thr Thr Pro Cys Ser Gly Ser Trp Leu Arg Asp Ile Trp Asp Trp Ile
        1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Lys
                2005                2010                2015

Gly Val Trp Arg Val Asp Gly Ile Met His Thr Arg Cys His Cys Gly
                2020                2025                2030

Ala Glu Ile Thr Gly His Val Lys Asn Gly Thr Met Arg Ile Val Gly
                2035                2040                2045

Pro Arg Thr Cys Arg Asn Met Trp Ser Gly Thr Phe Pro Ile Asn Ala
        2050                2055                2060

Tyr Thr Thr Gly Pro Cys Thr Pro Leu Pro Ala Pro Asn Tyr Thr Phe
2065                2070                2075                2080

Ala Leu Trp Arg Val Ser Ala Glu Glu Tyr Val Glu Ile Arg Gln Val
                2085                2090                2095

Gly Asp Phe His Tyr Val Thr Gly Met Thr Thr Asp Asn Leu Lys Cys
                2100                2105                2110

Pro Cys Gln Val Pro Ser Pro Glu Phe Phe Thr Glu Leu Asp Gly Val
        2115                2120                2125

Arg Leu His Arg Phe Ala Pro Pro Cys Lys Pro Leu Leu Arg Glu Glu
        2130                2135                2140

Val Ser Phe Arg Val Gly Leu His Glu Tyr Pro Val Gly Ser Gln Leu
2145                2150                2155                2160

Pro Cys Glu Pro Glu Pro Asp Val Ala Val Leu Thr Ser Met Leu Thr
                2165                2170                2175

Asp Pro Ser His Ile Thr Ala Glu Ala Ala Gly Arg Arg Leu Ala Arg
                2180                2185                2190

Gly Ser Pro Pro Ser Val Ala Ser Ser Ser Ala Ser Gln Leu Ser Ala
        2195                2200                2205

Pro Ser Leu Lys Ala Thr Cys Thr Ala Asn His Asp Ser Pro Asp Ala
        2210                2215                2220

Glu Leu Ile Glu Ala Asn Leu Leu Trp Arg Gln Glu Met Gly Gly Asn
2225                2230                2235                2240

-continued

```
Ile Thr Arg Val Glu Ser Glu Asn Lys Val Val Ile Leu Asp Ser Phe
            2245                2250                2255

Asp Pro Leu Val Ala Glu Glu Asp Glu Arg Glu Ile Ser Val Pro Ala
            2260                2265                2270

Glu Ile Leu Arg Lys Ser Arg Arg Phe Ala Gln Ala Leu Pro Val Trp
            2275                2280                2285

Ala Arg Pro Asp Tyr Asn Pro Pro Leu Val Glu Thr Trp Lys Lys Pro
            2290                2295                2300

Asp Tyr Glu Pro Pro Val Val His Gly Cys Pro Leu Pro Pro Lys
2305                2310                2315                2320

Ser Pro Pro Val Pro Pro Arg Lys Lys Arg Thr Val Val Leu Thr
            2325                2330                2335

Glu Ser Thr Leu Ser Thr Ala Leu Ala Glu Leu Ala Thr Arg Ser Phe
            2340                2345                2350

Gly Ser Ser Ser Thr Ser Gly Ile Thr Gly Asp Asn Thr Thr Thr Ser
            2355                2360                2365

Ser Glu Pro Ala Pro Ser Gly Cys Pro Pro Asp Ser Asp Ala Glu Ser
            2370                2375                2380

Tyr Ser Ser Met Pro Pro Leu Glu Gly Glu Pro Gly Asp Pro Asp Leu
2385                2390                2395                2400

Ser Asp Gly Ser Trp Ser Thr Val Ser Ser Glu Ala Asn Ala Glu Asp
            2405                2410                2415

Val Val Cys Cys Ser Met Ser Tyr Ser Trp Thr Gly Ala Leu Val Thr
            2420                2425                2430

Pro Cys Ala Ala Glu Glu Gln Lys Leu Pro Ile Asn Ala Leu Ser Asn
            2435                2440                2445

Ser Leu Leu Arg His His Asn Leu Val Tyr Ser Thr Thr Ser Arg Ser
            2450                2455                2460

Ala Cys Gln Arg Gln Lys Lys Val Thr Phe Asp Arg Leu Gln Val Leu
2465                2470                2475                2480

Asp Ser His Tyr Gln Asp Val Leu Lys Glu Val Lys Ala Ala Ala Ser
            2485                2490                2495

Lys Val Lys Ala Asn Leu Leu Ser Val Glu Glu Ala Cys Ser Leu Thr
            2500                2505                2510

Pro Pro His Ser Ala Lys Ser Lys Phe Gly Tyr Gly Ala Lys Asp Val
            2515                2520                2525

Arg Cys His Ala Arg Lys Ala Val Thr His Ile Asn Ser Val Trp Lys
            2530                2535                2540

Asp Leu Leu Glu Asp Asn Val Thr Pro Ile Asp Thr Thr Ile Met Ala
2545                2550                2555                2560
```

-continued

```
Lys Asn Glu Val Phe Cys Val Gln Pro Glu Lys Gly Gly Arg Lys Pro
            2565                2570                2575

Ala Arg Leu Ile Val Phe Pro Asp Leu Gly Val Arg Val Cys Glu Lys
        2580                2585                2590

Met Ala Leu Tyr Asp Val Val Thr Lys Leu Pro Leu Ala Val Met Gly
            2595                2600                2605

Ser Ser Tyr Gly Phe Gln Tyr Ser Pro Gly Gln Arg Val Glu Phe Leu
            2610                2615                2620

Val Gln Ala Trp Lys Ser Lys Lys Thr Pro Met Gly Phe Ser Tyr Asp
2625                2630                2635                2640

Thr Arg Cys Phe Asp Ser Thr Val Thr Glu Ser Asp Ile Arg Thr Glu
            2645                2650                2655

Glu Ala Ile Tyr Gln Cys Cys Asp Leu Asp Pro Gln Ala Arg Val Ala
            2660                2665                2670

Ile Lys Ser Leu Thr Glu Arg Leu Tyr Val Gly Gly Pro Leu Thr Asn
            2675                2680                2685

Ser Arg Gly Glu Asn Cys Gly Tyr Arg Arg Cys Arg Ala Ser Gly Val
            2690                2695                2700

Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Cys Thr Met Leu Val Cys
            2725                2730                2735

Gly Asp Asp Leu Val Val Ile Cys Glu Ser Ala Gly Val Gln Glu Asp
            2740                2745                2750

Ala Ala Ser Leu Arg Ala Phe Thr Glu Ala Met Thr Arg Tyr Ser Ala
            2755                2760                2765

Pro Pro Gly Asp Pro Pro Gln Pro Glu Tyr Asp Leu Glu Leu Ile Thr
            2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
            2805                2810                2815

Trp Glu Thr Ala Arg His Thr Pro Val Asn Ser Trp Leu Gly Asn Ile
            2820                2825                2830

Ile Met Phe Ala Pro Thr Leu Trp Ala Arg Met Ile Leu Met Thr His
            2835                2840                2845

Phe Phe Ser Val Leu Ile Ala Arg Asp Gln Leu Glu Gln Ala Leu Asp
            2850                2855                2860

Cys Glu Ile Tyr Gly Ala Cys Tyr Ser Ile Glu Pro Leu Asp Leu Pro
2865                2870                2875                2880
```

```
Pro Ile Ile Gln Arg Leu His Gly Leu Ser Ala Phe Ser Leu His Ser
            2885                2890                2895

Tyr Ser Pro Gly Glu Ile Asn Arg Val Ala Ala Cys Leu Arg Lys Leu
            2900                2905                2910

Gly Val Pro Pro Leu Arg Ala Trp Arg His Arg Ala Arg Ser Val Arg
            2915                2920                2925

Ala Arg Leu Leu Ala Arg Gly Gly Arg Ala Ala Ile Cys Gly Lys Tyr
            2930                2935                2940

Leu Phe Asn Trp Ala Val Arg Thr Lys Leu Lys Leu Thr Pro Ile Ala
2945                2950                2955                2960

Ala Ala Gly Gln Leu Asp Leu Ser Gly Trp Phe Thr Ala Gly Tyr Ser
            2965                2970                2975

Gly Gly Asp Ile Tyr His Ser Val Ser His Ala Arg Pro Arg Trp Ile
            2980                2985                2990

Trp Phe Cys Leu Leu Leu Leu Ala Ala Gly Val Gly Ile Tyr Leu Leu
            2995                3000                3005

Pro Asn Arg
    3010
```

FUSION POLYPEPTIDE HAVING THE C PROTEIN AND E1 PROTEIN OF HEPATITIS C VIRUS

RELATED APPLICATION(S)

This application is a Continuation-In-Part of and claims priority to PCT/FR98/00448, filed on Mar. 6, 1998, which claims priority to French application 97/02,887, filed on Mar. 6, 1997, the entire teachings of which are incorporated herein by reference.

BACKGROUND OF THE INVENTION

The invention relates to a pharmaceutical composition intended for the treatment or prophylaxis of infections induced by the hepatitis C virus (HCV).

The hepatitis C virus (HCV) is the agent responsible for the majority of hepatitis infections of the non-A non-B type. The seroprevalence of HCV infections varies between 0.3 and 1.5% in the world population, possibly reaching 18% in some developing countries. Hundreds of millions of people are thus thought to be infected worldwide. Nine types and thirty subtypes of HCV have been described. The subtypes may be associated with a defined geographical distribution, type 1b being the most widespread worldwide. The progression to the chronic form occurs in 50% of cases, about 5 years after the primary infection. Persistent Chronic Hepatitis which is asymptomatic, but which exhibits a high circulating virus titer, is first observed, then Active Chronic Hepatitis becomes established. Twenty percent of chronic hepatites progress to sclerosis of the liver within about ten years. Hepatocarcinoma may develop in the cirrhotic liver.

The hepatitis C virus (HCV) is a positive single-stranded RNA virus. On the basis of structural resemblance, HCV has been linked to the flavivirus and pestivirus families.

SUMMARY OF THE INVENTION

The present invention relates to fusion polypeptide that comprises a first region having the C polypeptide of the hepatitis C virus (HCV) or a portion thereof that comprises a polypeptide region responsible for gene regulatory activity; and a second region having the envelope polypeptide (E1) of the virus or a portion thereof that comprises a site for cytoplasmic anchorage of the E1 polypeptide, wherein the first region is fused by a peptide bond to the second region, and the fusion polypeptide is not cleaved by a mammalian protease.

The present invention also relates to a fusion polypeptide comprising a C polypeptide of HCV or a portion thereof and an E1 envelope polypeptide of HCV or a portion thereof. The C polypeptide comprises a first C polypeptide region responsible for gene regulatory activity and a second C polypeptide region responsible for the interaction with the E1 envelope polypeptide, wherein the site of interaction with the E1 polypeptide is between about 151 and about 173, or between about 173 and about 191. The E1 envelope polypeptide comprises a first E1 polypeptide region responsible for E1 cytoplasmic anchorage and a second E1 polypeptide region responsible for the interaction of the second C polypeptide region. The site for interaction with the C polypeptide is between about amino acid 330 and about amino acid 380. The C polypeptide is fused by a peptide bond to the E1 envelope polypeptide, and the C polypeptide comprises Cysteine$_{172}$Serine$_{173}$-Phenylalanine$_{174}$-Serine$_{175}$ with at least one mutation between amino acid Nos 172 and 175.

BRIEF DESCRIPTION OF THE FIGURES

FIGS. 4A–4L are an illustration of the nucleic acid sequence (SEQ ID NO.:1) and amino acid sequence (SEQ ID NO.:2) of HCV.

DETAILED DESCRIPTION OF THE INVENTION

Figure 1:
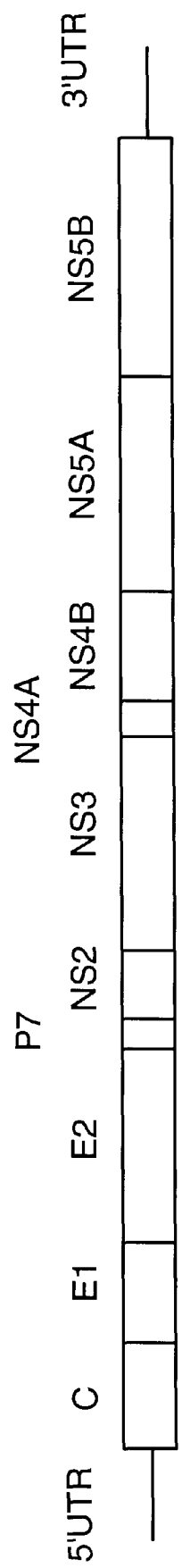
FIG. 1 is a schematic representation of the HCV genome which consists of RNA with its untranslated 5' and 3' regions indicated by lines, and the open reading frame of the precursor polyprotein indicated in the form of a rectangle.

During an infectious event, the HCV genome is first translated into a precursor polyprotein of about 3000 amino acids. This polyprotein then undergoes post-translational cleavages to give various precursors and mature viral proteins. The structural proteins of HCV are located in the N-terminal region of the polyprotein. As shown in FIG. 1, they are more particularly the capsid or core protein (C), and the envelope proteins E1 and E2, which are present in the following order: NH2-C-E1-E2. This portion is cleaved by the host cell proteases.

The numbering of the amino acids of the polyprotein as well as of its derivatives, which is adopted here after, is that commonly used and in particular presented by Choo et al., PNAS [vol. 88: p.2451 (1991)]. Thus, the C protein corresponds to the amino acids at positions 1 to 191 of the polyprotein and the E1 protein to the amino acids at positions 192 to 380. In the remainder of the text, it is appropriate to number the amino acids of the sequence of the E1 protein, from position 192 to position 380, 381, 382 or 383. In the remainder of the text, for the sake of simplicity, reference is made solely to the C-terminal position 380.

The C protein derived from the direct cleavage of the polyprotein contains 191 amino acids. This C protein, also called C191, may itself be truncated toward its C-terminal end by enzymatic cleavage to give a protein of 173 amino acids, called C173. In the remainder of the text, the term "C protein or polypeptide" will preferably designate the C191 form.

The C protein is a good vaccine candidate since it is of course a structural protein of the virus and since the region encoding this protein is relatively well conserved by the various HCV strains. It is known that a region of the C protein capable of generating a high antibody response corresponds to the first 120 amino acids; the first 48 amino acids constituting the major antigenic domain. However, a major obstacle to its use as vaccine lies in the fact that this protein is capable of transactivating genes belonging to the host cell, in particular genes such as oncogenes, which may have, inter alia, the consequence of inducing a carcinogenesis event.

Indeed, it has in particular been shown that the C173 form was capable of translocation in the nucleus of the host cell and of transactivation. The region of the C protein responsible for the translocation in the nucleus and for the regulatory activity appears to be located in the N-terminal portion (first 123 amino acids).

Thus, the region of the C protein which is of interest from a vaccine point of view is, on the other hand, responsible for a toxic effect toward the host cell.

To overcome this difficulty, a solution commonly envisaged in the scientific community would be to use a C191 protein whose cleavage site at position 173/174 would have been made inoperative by mutation. As will be seen below, such a protein nevertheless proves capable of regulatory activity, even if it is to a lesser degree.

Surprisingly, it has now been demonstrated that it was possible to abolish the regulatory activity of the C protein by modifying it and by combining it, under certain conditions, with the E1 protein. The present invention provides means for abolishing the regulatory activity by preventing the migration of the C protein into the nucleus. This migration no longer takes place in the presence of the E1 protein which possesses, inter alia, the property of becoming anchored in the cytoplasm, at the level of the endoplasmic reticulum, and which, unexpectedly, has the capacity to retain the C protein therein when certain conditions are met. The migration may be abolished by producing, for example, a fusion of the two proteins, cleavable or otherwise; in the case where it is cleavable, the products generated should be capable of interacting with each other so that there is no leakage of one of them into the nucleus; the complex formed by the product of cleavage being capable of becoming anchored in the cytoplasm. The equivalent of a cleavable peptide fusion is a mixture, in equimolar quantity, of the components constituting the fusion.

Accordingly, the subject of the invention is a pharmaceutical composition comprising:
(i) A polypeptide which contains:
(a) a first region corresponding to all or part of the C polypeptide of the hepatitis C virus; and
(b) a second region corresponding to all or part of the E1 polypeptide of said virus and,
proves, as such or via its products of cleavage, incapable of regulatory activity toward one or more genes;
(ii) A mixture (preferably) in substantially equimolar quantity,
(a) of a first polypeptide containing a region which corresponds to all or part of the C polypeptide of HCV and
(b) of a second polypeptide containing a region corresponding to all or part of the E1 polypeptide of HCV; and
which proves incapable of regulatory activity toward one or more genes; or
(iii) A DNA molecule comprising a sequence encoding the polypeptide as described in (i) of the present claim, placed under the control of elements necessary for its expression in a mammalian cell; and
a pharmaceutically acceptable carrier or diluent.

According to another aspect of the invention, the subject of the invention is also a method for the treatment or prevention of an infection induced by HCV according to which a pharmaceutical composition according to the invention is administered to a mammal, preferably a human, requiring such a treatment.

"Polypeptide" is understood to mean any chain of amino acids covalently linked to each other, regardless of the length of the chain and regardless of the post-translational modifications which may take place such as, for example, a lipidation. It is also possible to use the term protein interchangeably.

"C polypeptide of HCV" is understood to mean in particular a C polypeptide which possesses the amino acid sequence as disclosed by Choo et al. as well as any other C polypeptide obtained from any other strain and whose sequence could differ from that of Choo et al. For example, it may represent the C polypeptides described by Takeuchi K et al. [Nucleic Acids Research 18:4626 (1990)], Houghton M et al. [Hepatology 14:381 (1991)], Delisse et al. [J. Hepatology, 13, suppl. 4 (1991)], Bukh J et al. [PNAS 91:8239 (1994)] and Hiroaki O et al. [Intervirology 37:68 (1994)].

"E1 polypeptide of HCV" is understood to mean in particular an E1 polypeptide which possesses the amino acid sequence as disclosed by Choo et al. as well as any other E1 polypeptide obtained from any other strain and whose sequence could differ from that of Choo et al. For example, it may represent the E1 polypeptides described in Hiroaki O et al. [Intervirology 37:68 (1994)], Grakoui et al. [J. Virol. 67:1385 (1993)] and Spaete et al. [Virology 188:819 (1992)], Matsumia et al. [J. Virol. 66:1425] or in Kohara et al. [J. Gen. Virol. 73:2313 (1992)].

Thus, the amino acid sequence of the C polypeptide and that of the E1 polypeptide of HCV may vary according to the viral strain, reflecting the phenomenon of allelic variance. For example, a virus is usually represented by a set of strains which differ from each other in minor allelic characteristics. A polypeptide which fulfills the same biological function in different strains may have an amino acid sequence which is not the same for all the strains. Such an allelic variation is also found at the level of the DNA.

At the level of the amino acid sequence, the allelic differences may consist of one or more amino acid substitutions, deletions or additions which do not alter the biological function.

As regards the polypeptide included in the pharmaceutical composition according to the invention, two cases must be envisaged: either the polypeptide is incapable of being cleaved by a protease in a mammalian cell, or it is susceptible to such a cleavage.

When the polypeptide is incapable of being cleaved by a protease in a mammalian cell, it advantageously contains:
(a) a first region corresponding at least to the portion of the C polypeptide of the HCV virus responsible for the regulatory activity of said C polypeptide toward one or more genes; and
(b) a second region corresponding at least to a portion of the E1 polypeptide of said virus responsible for the cytoplasmic anchorage of the E1 polypeptide.

When the polypeptide is capable of being cleaved by a protease in a mammalian cell, it advantageously contains:
(a) a first region corresponding at least to a portion of the C polypeptide of HCV responsible for the regulatory activity of said C polypeptide toward one or more genes and to the portion of said C polypeptide responsible for the interaction of said C polypeptide with the E1 polypeptide of said virus; and
(b) a second region corresponding at least to a portion of the E1 polypeptide of said virus responsible for the interaction of the E1 polypeptide with the C polypeptide of said virus and to a portion of the E1 polypeptide of said virus responsible for the cytoplasmic anchorage of the E1 polypeptide.

"Portion of the C polypeptide of HCV responsible for the regulatory activity of said C polypeptide toward one or more genes" is understood to mean in particular any portion of the C polypeptide of HCV capable of activating, transactivating or suppressing the transcription or the expression of any gene, according to any mechanism. This gene may be a eukaryotic gene, a viral gene, an oncogene or a protooncogene.

A portion of the C polypeptide of HCV responsible for the regulatory activity of said polypeptide may in particular correspond to the amino acids at positions 38 to 43, 58 to 64, 66 to 71, 6 to 23, 39 to 74, 99 to 102, 101 to 121, 101 to 122, 58 to 121, 1 to 120, 1 to 121, 1 to 122, 1 to 123 or 1 to 173. Preferably, a portion of the C polypeptide of HCV responsible for the regulatory activity may be a portion of the C polypeptide ranging from the amino acid at position 1 to the amino acid in one of positions 48 to 191. For this purpose, one of positions 48 to 191 may be for example position 119, 120, 121, 123 and 173.

A portion of the C polypeptide of HCV responsible for the interaction of said C polypeptide with the E1 protein of HCV may in particular correspond to the amino acids at positions 151 to 173 or at positions 173 to 191 of the C polypeptide of HCV.

A portion of the E1 polypeptide of HCV responsible for the cytoplasmic anchorage of the E1 polypeptide may be a hydrophobic domain of the E1 polypeptide. Such hydrophobic domains are for example located at positions 262 to 291, 370 to 380 and 330 to 380 of the E1 polypeptide.

A portion of the E1 polypeptide of HCV responsible for the interaction of the C polypeptide with the E1 protein may be in particular the C-terminal domain of the E1 polypeptide, preferably the domain at positions 330 to 380 or at positions 370 to 380.

In a polypeptide useful for the purposes of the present invention, the first region may be located on the N- or C-terminal side of the polypeptide, advantageously on the N-terminal side; likewise, the second region may be located on the C- or N-terminal side, advantageously on the C-terminal side. According to a preferred mode, the C-terminal end of the first region may be fused by peptide bonding to the N-terminal end of the second region.

When the polypeptide contained in the pharmaceutical composition according to the invention comprises the region corresponding at least to the amino acids at positions 172 to 175 of the C polypeptide of HCV, this polypeptide advantageously contains a mutation making the cleavage site at position 173/174 inoperative. According to a preferred mode, such a mutation is a point mutation, carried out in one of positions 172 to 175. It may be obtained, for example, by deletion, addition or substitution of one or more amino acids, in particular by deletion, addition or substitution of one or more amino acid at positions 172 to 175. Preferably the mutation will be produced by substitution of one or two amino acids; a double mutation by substitution being most particularly preferred. According to a particular example, the residue naturally existing at position 173 (serine) may be in particular substituted by the methionine residue and the residue naturally existing at position 173 (phenylalanine) may be substituted in particular by the leucine residue. In general, it is within the capability of persons skilled in the art to produce one or more mutations capable of making inoperative the cleavage site at position 173/174 of the C polypeptide of HCV.

When the polypeptide contained in the pharmaceutical composition according to the invention comprises the region corresponding at least to the amino acids at positions 190 to 193 of the HCV polyprotein, this polypeptide advantageously contains a mutation making inoperative the cleavage site at position 191/192 of the HCV polyprotein. According to a preferred mode, such a mutation is a point mutation produced in one of positions 190 to 193. It may be obtained, for example, by deletion, addition or substitution of one or more amino acids, in particular by deletion, addition or substitution of one or more amino acids at positions 190 to 193. Preferably, the mutation will be produced by substitution of one or two amino acids, a double mutation by substitution being most particularly preferred. According to a specific example, the residue naturally existing at position 191 (alanine) may in particular be substituted by the valine residue and the residue naturally existing at position 192 (tyrosine) may in particular be substituted by the asparagine residue. In general, it is within the capability of persons skilled in the art to produce one or more mutations capable of making inoperative the cleavage site at position 191/192.

When the polypeptide useful for the purposes of the present invention comprises both the region corresponding at least to amino acids 190 to 193 of the HCV polyprotein and the region corresponding at least to amino acids 172 to 175 of the C polypeptide of HCV, only one of the two cleavage sites 191/192 and 173/174 can be made inoperative, preferably both will be made inoperative. When only the site 173/174 is made inoperative, the polypeptide is capable of being cleaved and in this particular case, it is necessary that this polypeptide possesses a first region which corresponds, inter alia, to the portion of the C polypeptide responsible for the interaction of said polypeptide with the E1 polypeptide and a second region which corresponds, inter alia, to the portion of the E1 polypeptide responsible for the interaction of said polypeptide with the C polypeptide.

When a polypeptide useful for the purposes of the present invention is incapable of being cleaved by a protease, it may contain a cleavage site on the condition, however, that this cleavage site is not functional. For example, in the particular case of a polypeptide consisting of the C191 polypeptide fused with the E1 polypeptide and containing a mutation making inoperative the cleavage site at position 191/192, the cleavage site at position 173/174 may not be mutated; however, it will not be, or will be only slightly, functional, insofar as the cleavage at position 191/192 is no longer possible. Indeed, it is known that the cleavage at position 191/192 must be carried out for the cleavage at position 173/174 to take place.

According to a specific mode, a polypeptide useful for the purposes of the present invention is incapable of being cleaved by a protease and contains:

(a) a first region which substantially corresponds to the domain of the C polypeptide ranging from the amino acid at position 1 to the amino acid in one of positions 120 to 173, and (b) a second region which substantially corresponds to a domain of the E1 polypeptide containing at least one hydrophobic region, for example to the domain of the E1 polypeptide ranging from the amino acid at position 192 to the amino acid at position 380, or from the amino acid at position 330 to the amino acid at position 380, or from the amino acid at position 260 to the amino acid at position 290, or from the amino acid at position 260 to the amino acid at position 380.

According to another particular mode, a polypeptide useful for the purposes of the present invention is incapable of being cleaved by a protease and contains:

(a) a first region which substantially corresponds to the domain of the C polypeptide ranging from the amino acid at position 1 to the amino acid in one of positions 120 to 191, and (b) a second region which substantially corresponds to a domain of the E1 polypeptide containing at least one hydrophobic region, for example to the domain of the E1 polypeptide ranging from the amino acid at position 192 to the amino acid at position 380, or from the amino acid at position 330 to the amino acid at position 380, or from the amino acid at position 260 to the amino acid at position 290, or from the amino acid at position 260 to the amino acid at position 380;

on the condition that said polypeptide does not contain a cleavage site 191/192 or alternatively when the cleavage site is reconstituted, then a mutation is introduced in order to make it inoperative.

Advantageously, the first region of the polypeptide useful for the purposes of the present invention corresponds to the amino acids at positions 1 to 191 of the C polypeptide of HCV and/or the second region of this polypeptide corresponds at least to the amino acids at positions 192 to 380 of the E1 polypeptide or HCV. In a particularly preferred manner, the first and second regions are as defined above in this same paragraph, the amino acid at position 191 being fused by peptide bonding to the amino acid at position 192. According to a particular mode, the polypeptide consists of the first and second regions as defined above in this same paragraph.

When the polypeptide useful for the purposes of the present invention is as described in the preceding paragraph, it imperatively contains a mutation making inoperative the cleavage site at position 191/192 or at position 173/174. Preferably, the two cleavage sites are made inoperative.

A mixture useful for the purposes of the present invention advantageously comprises:

(a) a first polypeptide containing a region which corresponds at least to the portion of the C polypeptide of the HCV virus responsible for the regulatory activity of said C polypeptide toward one or more genes and to the portion of said C polypeptide responsible for the interaction of said C polypeptide with the E1 polypeptide of said virus, and (b) a second polypeptide containing a region corresponding to a portion of the E1 polypeptide of said virus responsible for the interaction of the E1 polypeptide with the C polypeptide of said virus and to a portion of the E1 polypeptide of said virus responsible for the cytoplasmic anchorage of the E1 polypeptide.

The portions of the C and E1 polypeptides responsible for the properties listed in points (a) and (b) of the preceding paragraph may be as described above for the fusion polypeptide.

Preferably, the first polypeptide of the mixture contains and in a most particularly preferred manner consists of a region corresponding to the amino acids at positions 1 to 191 of the C polypeptide (C191) of HCV. In the latter case, the cleavage site at position 173/174 must be made inoperative by mutation. This mutation may be produced as described above for the fusion polypeptide.

Preferably, the second polypeptide of the mixture contains and in a most particularly preferred manner consists of a region corresponding to the amino acids at positions 192 to 380 of the E1 polypeptide of HCV.

For the purposes of the present invention, a DNA molecule may be a simple linear DNA fragment, or alternatively a plasmid or alternatively a viral vector such as a pox vector.

A polypeptide, a mixture or a molecule of DNA as described in the present application are of a most special interest when they are used for the manufacture of a medicament intended for the treatment or prevention of infections induced by HCV. They are in particular useful in the immunotherapy of infections induced by HCV, most particularly a DNA molecule.

Finally, the invention relates to a method for inducing an immune response toward HCV in a mammal, according to which an immunologically effective quantity of a composition according to the invention is administered to said mammal in order to develop an immune response. The invention also relates to a method for the prevention or treatment of an infection induced by HCV, according to which a prophylactically or therapeutically effective quantity of a composition according to the invention is administered to an individual.

The methods and the pharmaceutical compositions according to the invention can treat or prevent HCV infections and consequently hepatic diseases associated with such infections. They are in particular persistent chronic hepatitis, active chronic hepatitis, cirrhosis of the liver and hepatocarcinomas.

A composition according to the invention may be administered by any conventional route used in the field of vaccines, in particular by the parenteral (e.g. subcutaneous, intradermal, intramuscular, intravenous or intraperitoneal) route. The choice of the route of administration depends on a number of parameters such as the nature of the active principle, polypeptide or DNA molecule, the adjuvant combined with the polypeptide or with the DNA molecule.

A composition according to the invention may comprise, in addition to a polypeptide or a mixture of polypeptides useful for the purposes of the present invention, at least one other HCV antigen such as the E2 protein or alternatively such as a nonstructural protein NS1, NS2, NS3, NS4 or NS5, or a subunit, fragment, homolog, mutant or derivative of these antigens.

A polypeptide, a mixture or a molecule of DNA useful for the purposes of the present invention may be formulated in or with liposomes, preferably neutral or anionic liposomes, microspheres ISCOMs or virus-like particles (VLPs), in order to promote the screening of the protein or of the polypeptide or to increase the immune response. Persons skilled in the art have these compounds available without difficulty; for example see Liposomes: A Practical Approach. RRC New ED, IRL press (1990).

Adjuvants other than liposomes may also be used. A large number are known to persons skilled in the art. Such adjuvants are identified by references below:

For parenteral administration, there may be mentioned in particular aluminum compounds such as aluminum hydroxide, aluminum phosphate and aluminum hydroxyphosphate. The antigen may be absorbed or precipitated on an aluminum compound according to standard methods. Other adjuvants useful for parenteral administration include in particular polyphosphazene (WO 95/2415), DC-chol (3-beta-[N-(N', N'-dimethylaminomethane)carbamoyl] cholesterol) (U.S. Pat. No. 5,283,185 and WO 96/14831), QS-21 (WO 88/9336) and RIBI from ImmunoChem (Hamilton, Mont.).

The administration may take place in a single dose or in a dose repeated once or several times after a certain period. The appropriate dosage varies according to various parameters, for example the individual treated (adult or child), the vaccinal antigen itself, the mode and frequency of administration, the presence or absence of adjuvant and, if present, the type of adjuvant and the desired effect (e.g. protection or treatment), as will be determined by persons skilled in the art.

A composition according to the invention may be manufactured conventionally. In particular, a polypeptide, a mixture or a molecule of DNA contained in the composition according to the invention is combined with a pharmaceutically acceptable diluent or carrier, e.g. water or a saline solution such as phosphate-buffered saline (PBS). In general, the diluent or the carrier is selected on the basis of the mode and route of administration and of standard pharmaceutical practices. Pharmaceutically acceptable diluents and carriers as well as all that is necessary for their use in pharmaceutical formulations are described in Remington's Pharmaceutical Sciences, a standard reference text in this field and in USP/NP.

EXEMPLIFICATION

EXAMPLE 1

Construction of Recombinant Plasmids and Site-Directed Mutagenesis

Figure 2:
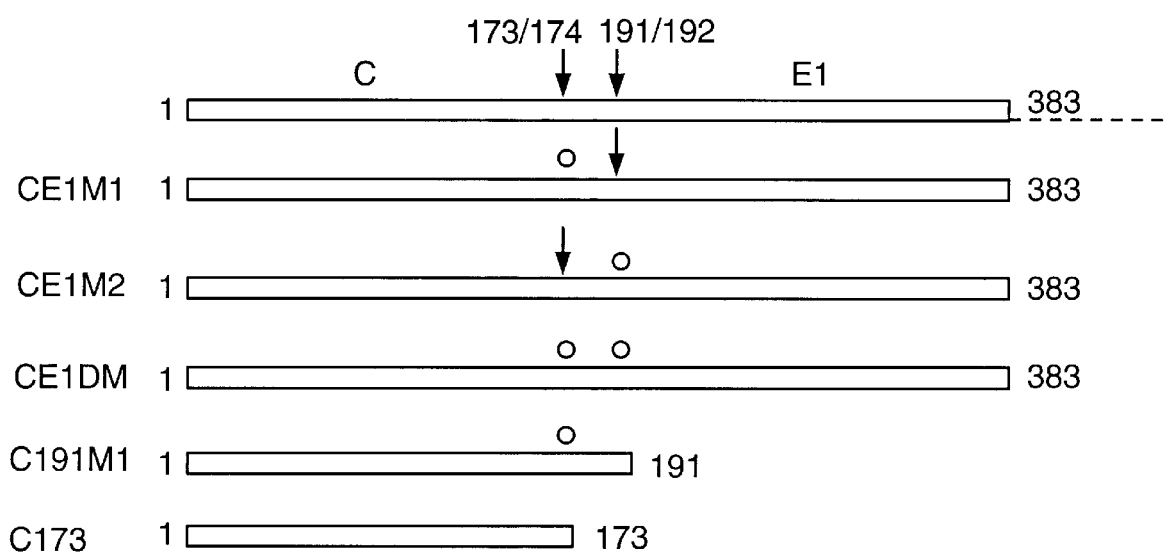
FIG. 2 represents the inserts derived from the HCV genome which are tested in plasmids pRC. The sequences derived from the HCV genome are represented by a rectangle and the mutated residues are indicated by dots.
Figure 3:
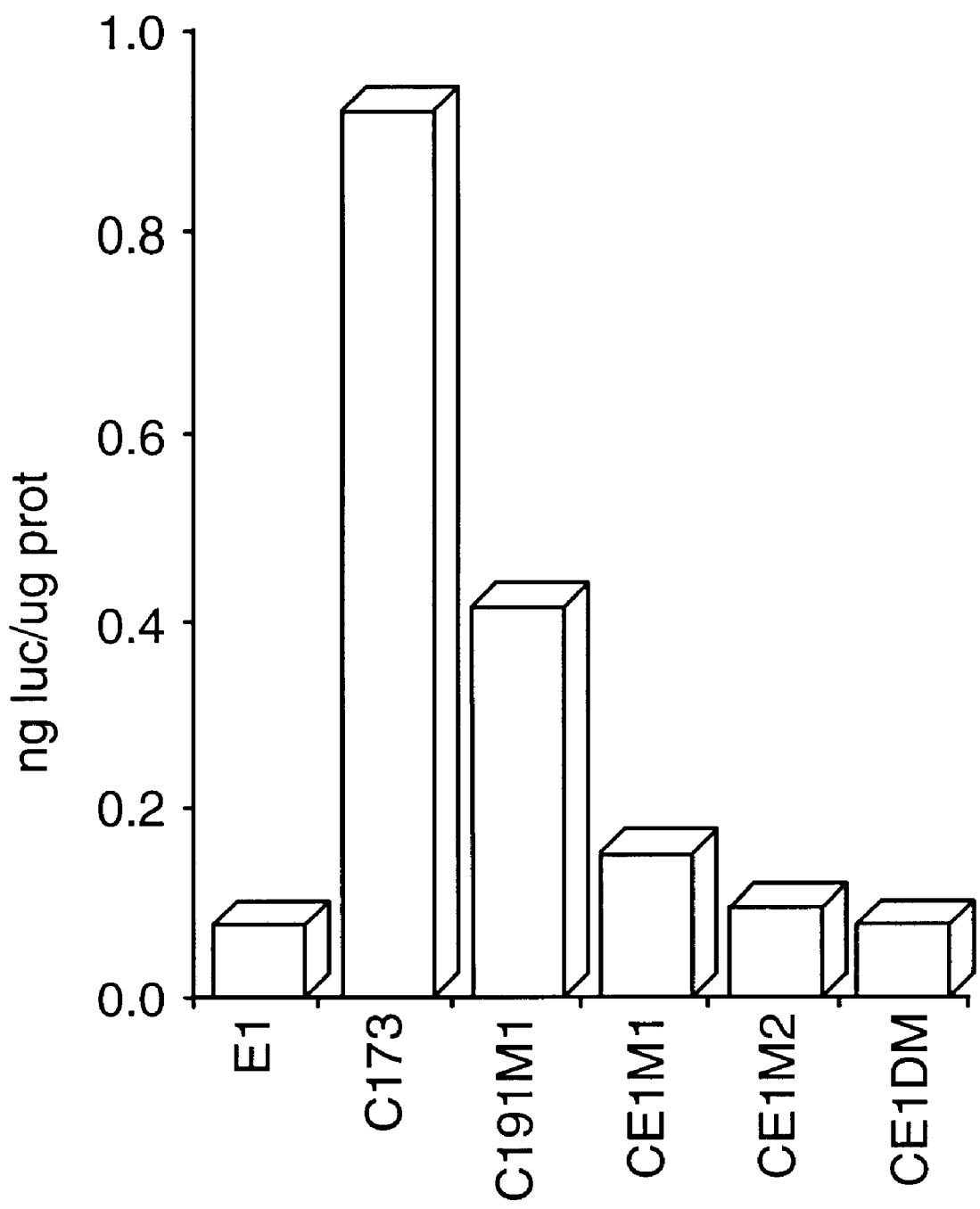
FIG. 3 is a diagram representing the luciferase activity measured for each of the constructs of which some are mutated at the level of one or more cleavage sites. The identity of the insert tested appears on the x-axis while the quantity of luciferase produced relative to the total quantity of protein produced appears on the y-axis.

The constructs called pRC/E1, pRC/CE1M1, pRC/CE1M2 and pRC/CE1M1M2 (also call pRC/CE1DM), pRC/C191M1 and pRC/C173, which are used below in Example 2, have been described in: Liu Q et al., J. Virol. 71: 657 (1997). The inserts used are represented in FIG. 2. All the constructs are produced in the vector pRC which is obtained from InVitrogen (ref: V780-20). The vector pRC carries the ampicillin gene and allows the expression of inserts under the control of a CMV promoter. Mutations called M1 and M2 are present in the constructs pRC/C191M1, pRC/CE1M1, pRC/CE1M2 and pRC/CE1M1M2. They were generated by site-directed mutagenesis performed by PCR. The mutation called M1 corresponds to the replacement of the amino acids Serine$^{173}$ and Phe$^{174}$ of the C protein with the amino acids methionine and leucine, respectively. The mutation called M2 corresponds to the replacement of the amino acids alanine$^{191}$ and tyrosine$^{192}$ of the CE1 protein with the amino acids valine and asparagine, respectively.

The plasmids expressing the reporter genes for luciferase and for β-galactosidase were constructed by modifying the vector pUC 18 (Appligene; ref: 161131). The expression of the genes is under the control of the immediate-early promoter 1(ie1) of the human CMV. Sequences derived from the 3' region of the bovine gene for the growth hormone were moreover added in the 3' of the genes in order to stabilize the mRNAs. These plasmids carry more than one ampicillin gene.

EXAMPLE 2

Transfection of Cells with the Plasmids

CHO-K1 cells (ATCC CCL 61) were stored in α-MEM medium [Nature 230:310 (1971)], supplemented with 10% Foetal Calf Serum (FCS) (Hyclone, ref:A1115-L) and 20% Dimethyl Sulfoxide (DMSO) in liquid nitrogen. These cells are cultured under humid atmosphere at 37° C. with 5% $CO_2$ and 95% air. To carry out subcultures, the medium removed and the cellular lawn is rinsed with 5 ml of phosphate buffer (PBS). The supernatant is then removed before addition of 1.5 ml of trypsin per 75 cm$^2$ flask (trypsin at 0.025%). After incubating for 10 min in an incubator at 37° C., the reaction is stopped by addition of 10 ml of α-MEM medium containing 10% FCS. The cells are counted on a Malassez cell after a one-half dilution in 0.02% Trypan blue. $5 \times 10^5$ cells are then inoculated into dishes 6 cm in diameter with complete medium.

The CHO cells are then cotransfected with one of the recombinant plasmids (pHCV) described above and a reporter plasmid (pCMV) which contains either the β-galactosidase gene under the control of the CMV promoter (pCMV β-gal) or the luciferase gene under the control of the CMV promoter (pCMV Luc).

For that, 5 μg of DNA (4.5 μg of plasmid pHCV/0.5 μg of plasmid pCMV) are diluted in 500 μl of OPTI-MEM medium (Gibco), and mixed with 14 μl of lipofectamine diluted in 500 μl of the same medium. The two solutions are mixed and incubated for 20 min at room temperature in order to allow the formation of the DNA-liposome complexes.

The DNA liposome mixture diluted with 2 ml of OPTI-MEM is then added to the cells after removing the culture medium and rinsing in PBS. After incubating for 5 hours, the medium is again changed and 48 h after the transfection, it is then possible to test for the transient expression of the recombinant genes.

EXAMPLE 3

Demonstration of the Regulatory Activity of the Constructs on Reporter Genes

The transfected cells are lysed with the aid of the reagent "Luciferase Cell Culture Lysis Reagent" (Promega, Luciferase Assay System). 100 μl of substrate are added to 100 μl of cell supernatant, directly by the bioluminometer injector (Lumat LB/9501/16 from Berthold) which measures the quantity of light emitted (Relative Light Units) for 10 seconds. The quantity of light emitted is then converted to nanograms of proteins per ml of cell lysate, by comparing with a standard curve established with the aid of purified luciferase.

The results, which are presented in FIG. 2, show that a point mutation at the amino acid 191 in the construct CE1M2 abolishes the transactivating effect. A point mutation at the amino acid 173 (in the construct CE1M1) abolishes the transactivating effect only in the case where C is fused with E1. A double mutation at the amino acids 173 and 191 abolishes the transactivating effect.

The teachings of all the articles, patents, and patent applications cited herein are incorporated by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A fusion polypeptide that comprises:
 (a) a first region consisting essentially of the C polypeptide of the hepatitis C virus (HCV) or a portion thereof that comprises a polypeptide region responsible for gene regulatory activity; and
 (b) a second region consisting essentially of the envelope polypeptide (E1) of the virus or a portion thereof that comprises a site for cytoplasmic anchorage of the E1 polypeptide;
wherein the first region is fused by a peptide bond to the second region, and the fusion polypeptide is not cleaved by a mammalian protease.

2. The polypeptide of claim 1, wherein the first region comprises a C-terminal end, and the second region comprises a N-terminal end, and the C-terminal end of the first region is fused with peptide bond to the N-terminal end of the second region.

3. The fusion polypeptide of claim 2, wherein the fusion polypeptide does not contain the amino acid sequence $Serine_{190}$-$Alanine_{191}$-$Tyrosine_{192}$-Glutamic $acid_{193}$.

4. The fusion polypeptide of claim 3, that contains an amino acid sequence that corresponds to the amino acid sequence $Serine_{190}$-$Alanine_{191}$-$Tyrosine_{192}$-Glutamic $acid_{193}$ wherein the Alanine residue is substituted by a Valine residue or wherein the Tyrosine residue is substituted by an Asparagine residue.

5. The fusion polypeptide of claim 1, wherein the amino acid sequence of the first region does not contain the amino acid sequence $Cysteine_{172}$-$Serine_{173}$-$Phenylalanine_{174}$-$Serine_{175}$.

6. The fusion polypeptide of claim 1, wherein the second region further comprises the amino acid sequence of polypeptide E1 from amino acid No. 194 to amino acid No. 380.

7. The fusion polypeptide of claim 1, wherein the second region further comprises an amino acid sequence selected in the group consisting of amino acid Nos 262 to 291, amino acid Nos 370 to 380, amino acid Nos 330 to 380 of the E1 envelope polypeptide.

8. The fusion polypeptide of claim 1, wherein the first region comprises the amino acid sequence of the C polypeptide from amino acid in position 1 to any amino acid in position 48 to 191.

9. The fusion polypeptide of claim 8, wherein the first region comprises the amino acid sequence of the C polypeptide from amino acid in position 1 to amino acid in position 120.

10. A fusion polypeptide comprising:

a) a C polypeptide of HCV or a portion thereof that comprises:
   1) a first C polypeptide region responsible for gene regulatory activity and
   2) a second C polypeptide region responsible for the interaction with the E1 envelope polypeptide, wherein the site of interaction with the E1 polypeptide is between about 151 and about 173, or between about 173 and about 191, and b) a E1 envelope polypeptide of HCV or a portion thereof that comprises:
   1) a first E1 polypeptide region responsible for E1 cytoplasmic anchorage and
   2) a second E1 polypeptide region responsible for the interaction of said second C polypeptide region, wherein the site for interaction with the C polypeptide is between about amino acid 330 and about amino acid 380;

wherein said C polypeptide is fused by a peptide bond to said E1 envelope polypeptide, and the C polypeptide comprises $Cysteine_{172}$-$Serine_{173}$-$Phenylalanine_{174}$-$Serine_{175}$ with at least one mutation between amino acid Nos 172 and 175.

11. The fusion polypeptide of claim 10, wherein the Serine residue in position 173 is substituted by a Methionine residue or wherein the Phenylalanine residue is substituted by a Leucine residue.

12. The fusion polypeptide of claim 10, wherein the C polypeptide contains a C terminal end and the E1 polypeptide contains a N terminal end, wherein the C terminal end is fused to the N terminal end and, wherein the fusion polypeptide contains the amino acid sequence $Serine_{190}$-$Alanine_{191}$-$Tyrosine_{192}$-$Glutamic\ acid_{193}$.

13. The fusion polypeptide of claim 10, wherein the E1 envelope polypeptide comprises the amino acid sequence of polypeptide E1 from amino acid in position 192 to amino acid in position 380.

14. The fusion polypeptide of claim 10, wherein the C polypeptide comprises the amino acid sequence of the C polypeptide from amino acid in position 1 to amino acid in position 171.

15. The fusion polypeptide of claim 14, wherein the C polypeptide further comprises the amino acid sequence of the C polypeptide from amino acid in position 176 to amino acid in position 191.

* * * * *